US012667607B2

(12) United States Patent (10) Patent No.: US 12,667,607 B2
Vijayan et al. (45) Date of Patent: Jun. 30, 2026

(54) METHODS OF REDUCING COLLAGENASE-MEDIATED BRUISING IN A SUBJECT HAVING CELLULITE

(71) Applicant: ENDO OPERATIONS LIMITED, Blanchardstown (IE)

(72) Inventors: Saji Vijayan, Downingtown, PA (US); David Hernandez, Lititz, PA (US); James Patrick Tursi, Moorestown, NJ (US)

(73) Assignee: Endo Operations Limited, Dublin (IE)

( * ) Notice: Subject to any disclaimer, the term of this patent is extended or adjusted under 35 U.S.C. 154(b) by 414 days.

(21) Appl. No.: 18/315,351

(22) Filed: May 10, 2023

(65) Prior Publication Data

US 2023/0405097 A1 Dec. 21, 2023

Related U.S. Application Data

(60) Provisional application No. 63/378,424, filed on Oct. 5, 2022, provisional application No. 63/340,295, filed on May 10, 2022.

(51) Int. Cl.
| | |
|---|---|
| *A61K 38/48* | (2006.01) |
| *A61K 9/00* | (2006.01) |
| *A61P 17/02* | (2006.01) |
| *A61P 19/04* | (2006.01) |

(52) U.S. Cl.
CPC ........ *A61K 38/4886* (2013.01); *A61K 9/0019* (2013.01); *A61P 17/02* (2018.01); *A61P 19/04* (2018.01); *C12Y 304/24007* (2013.01)

(58) Field of Classification Search
CPC .............. A61K 38/4886; A61K 9/0019; A61K 2800/91; A61K 8/41; A61K 8/42; A61K 8/66; A61K 31/137; A61K 31/167; A61P 17/02; A61P 19/04; C12Y 304/24007; A61Q 19/06
See application file for complete search history.

(56) References Cited

U.S. PATENT DOCUMENTS

| | | | |
|---|---|---|---|
| 7,374,551 B2 | 5/2008 | Liang et al. |
| 7,811,560 B2 | 10/2010 | Sabatino et al. |
| 9,744,138 B2 | 8/2017 | Leppert et al. |
| 9,757,435 B2 | 9/2017 | Herber |

FOREIGN PATENT DOCUMENTS

| | | |
|---|---|---|
| WO | 2007/100675 A2 | 9/2007 |
| WO | 2012/125948 A1 | 9/2012 |
| WO | 2020/021330 A2 | 1/2020 |
| WO | 2020/021332 A2 | 1/2020 |
| WO | 2020/058755 A1 | 3/2020 |

OTHER PUBLICATIONS

Auxilium Press release , Exhibit 99.1, 2011, p. 1-4. (Year: 2011).*
Goldman et al., "Phase 2a, randomized, double-blind, placebo-controlled dose-ranging study of repeat doses of collagenase clostridium histolyticum for the treatment of edematous fibrosclerotic panniculopathy (cellulite)", Journal of the American Academy of Dermatology, vol. 72, No. 5, May 2015, AB19.
Hexsel et al., "A validated photonumeric cellulite severity scale", Journal of the European Academy of Dermatology and Venereology, Feb. 2009, 7 pages.
Kaufman-Janette et al., "Collagenase Clostridium Histolyticum-aaes for the Treatment of Cellulite in Women: Results From Two Phase 3 Randomized, Placebo-Controlled Trials", Dermatol. Surg. 2021, 47(5), 649-656.
Nurnberger et al., "So-Called Cellulite: An Invented Disease", J. Dermatology Surgery Oncol., Mar. 1978, 221-229.
Qwo® (collagenase clostridium histolyticum-aaes) for injection, Package insert, Endo Aesthetics LLC, 2020, 11 pages.
Shridharani, Presented at: Vegas Cosmetic Surgery and Aesthetic Dermatology, Sep. 24-27, 2020, Virtual.

* cited by examiner

*Primary Examiner* — Kade Ariani
(74) *Attorney, Agent, or Firm* — BakerHostetler

(57) ABSTRACT

Disclosed herein are methods of reducing collagenase-mediated bruising in a subject having cellulite, methods of treating cellulite in a subject, and collagenase-containing formulations.

11 Claims, 6 Drawing Sheets

Specification includes a Sequence Listing.

FIG. 2

For each buttock (LEFT / RIGHT), the severity of bruising will be rated:

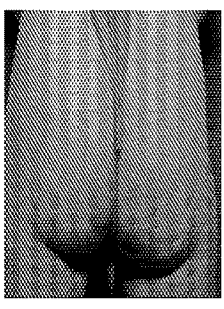 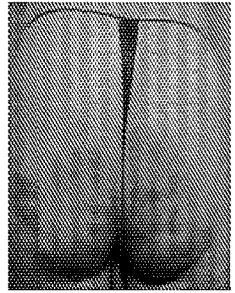 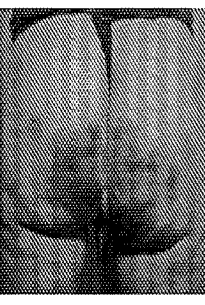 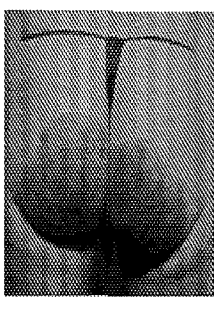 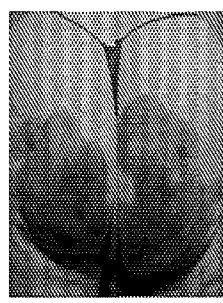

| 0 – None or almost none | 1 – Mild | 2 – Moderate | 3 – Severe | 4 – Very Severe |
|---|---|---|---|---|
| No bruising or almost no bruising observed | Mild intensity bruising, Pink-light red color, covering approximately 25% of the buttock | Moderate intensity bruising, deep red to purple color, covering approximately 50% of the buttock | Severe bruising, deep purple color, covering approximately 75% of the buttock | Severe bruising, deep to darkest purple color, covering approximately 100% of the buttock |

SEQUENCE LISTING

```
Sequence total quantity: 2
SEQ ID NO: 1              moltype = AA  length = 1008
FEATURE                  Location/Qualifiers
source                   1..1008
                         mol_type = protein
                         organism = Synthetic construct
SEQUENCE: 1
IANTNSEKYD FEYLNGLSYT ELTNLIKNIK WNQINGLFNY STGSQKFFGD KNRVQAIINA   60
LQESGRTYTA NDMKGIETFT EVLRAGFYLG YYNDGLSYLN DRNFQDKCIP AMIAIQKNPN  120
FKLGTAVQDE VITSLGKLIG NASANAEVVN NCVPVLKQFR ENLNQYAPDY VKGTAVNELI  180
KGIEFDFSGA AYEKDVKTMP WYGKIDPFIN ELKALGLYGN ITSATEWASD VGIYYLSKFG  240
LYSTNRNDIV QSLEKAVDMY KYGKIAFVAM ERITWDYDGI GSNGKKVDHD KFLDDAEKHY  300
LPKTYTFDNG TFIIRAGEKV SEEKIKRLYW ASREVKSQFH RVVGNDKALE VGNADDVLTM  360
KIFNSPEEYK FNTNINGVST DNGGLYIEPR GTFYTYERTP QQSIFSLEEL FRHEYTHYLQ  420
ARYLVDGLWG QGPFYEKNRL TWFDEGTAEF FAGSTRTSGV LPRKSILGYL AKDKVDHRYS  480
LKKTLNSGYD DSDWMFYNYG FAVAHYLYEK DMPTFIKMNK AILNTDVKSY DEIIKKLSDD  540
ANKNTEYQNH IQELADKYQG AGIPLVSDDY LKDHGYKKAS EVYSEISKAA SLTNTSVTAE  600
KSQYFNTFTL RGTYTGETSK GEFKDWDEMS KKLDGTLESL AKNSWSGYKT LTAYFTNYRV  660
TSDNKVQYDV VFHGVLTDNA DISNNKAPIA KVTGPSTGAV GRNIEFSGKD SKDEDGKIVS  720
YDWDFGDGAT SRGKNSVHAY KKTGTYNVTL KVTDDKGATA TESFTIEIKN EDTTTPITKE  780
MEPNDDIKEA NGPIVEGVTV KGDLNGSDDA DTFYFDVKED GDVTIELPYS GSSNFTWLVY  840
KEGDDQNHIA SGIDKNNSKV GTFKATKGRH YVFIYKHDSA SNISYSLNIK GLGNEKLKEK  900
ENNDSSDKAT VIPNFNTTMQ GSLLGDDSRD YYSFEVKEEG EVNIELDKKD EFGVTWTLHP  960
ESNINDRITY GQVDGNKVSN KVKLRPGKYY LLVYKYSGSG NYELRVNK            1008

SEQ ID NO: 2              moltype = AA  length = 991
FEATURE                  Location/Qualifiers
source                   1..991
                         mol_type = protein
                         organism = Synthetic construct
SEQUENCE: 2
AVDKNNATAA VQNESKRYTV SYLKTLNYYD LVDLLVKTEI ENLPDLFQYS SDAKEFYGNK   60
TRMSFIMDEI GRRAPQYTEI DHKGIPTLVE VVRAGFYLGF HNKELNEINK RSFKERVIPS  120
ILAIQKNPNF KLGTEVQDKI VSATGLLAGN ETAPPEVVNN FTPIIQDCIK NMDRYALDDL  180
KSKALFNVLA APTYDITEYL RATKEKPENT PWYGKIDGFI NELKKLALYG KINDNNSWII  240
DNGIYHIAPL GKLHSNNKIG IETLTEVMKI YPYLSMQHLQ SADQIERHYD SKDAEGNKIP  300
LDKFKKEGKE KYCPKTYTFD DGKVIIKAGA RVEEEKVKRL YWASKEVNSQ FFRVYGIDKP  360
LEEGNPDDIL TMVIYNSPEE YKLNSVLYGY DTNNGGMYIE PDGTFFTYER KAEESTYTLE  420
ELFRHEYTHY LQGRYAVPGQ WGRTKLYDND RLTWYEEGGA ELFAGSTRTS GILPRKSIVS  480
NIHNTTRNNR YKLSDTVHSK YGASFEFYNY ACMFMDYMYN KDMGILNKLN DLAKNNDVDG  540
YDNYIRDLSS NHALNDKYQD HMQERIDNYE NLTVPFVADD YLVRHAYKNP NEIYSEISEV  600
AKLKDAKSEV KKSQYFSTFT LRGSYTGGAS KGKLEDQKAM NKFIDDSLKK LDTYSWSGYK  660
TLTAYFTNYK VDSSNRVTYD VVFHGYLPNE GDSKNSLPYG KINGTYKGTE KEKIKFSSEG  720
```

```
SFDPDGKIVS YEWDFGDGNK SNEENPEHSY DKVGTYTVKL KVTDDKGESS VSTTTAEIKD  780
LSENKLPVIY MHVPKSGALN QKVVFYGKGT YDPDGSIAGY QWDFGDGSDF SSEQNPSHVY  840
TKKGEYTVTL RVMDSSGQMS EKTMKIKITD PVYPIGTEKE PNNSKETASG PIVPGIPVSG  900
TIENTSDQDY FYFDVITPGE VKIDINKLGY GGATWVVYDE NNNAVSYATD DGQNLSGKFK  960
ADKPGRYYIH LYMFNGSYMP YRINIEGSVG R                                991
```

METHODS OF REDUCING COLLAGENASE-MEDIATED BRUISING IN A SUBJECT HAVING CELLULITE

CROSS REFERENCE TO RELATED APPLICATIONS

This application claims priority to U.S. Provisional Application No. 63/378,424, which was filed on Oct. 5, 2022, and U.S. Provisional Application No. 63/340,295, which was filed on May 10, 2022, the disclosures of each of which are hereby incorporated by reference in their entirety.

SEQUENCE LISTING

The instant application contains a Sequence Listing, which is being submitted herewith electronically in XML format and is hereby incorporated by reference in its entirety. Said XML copy, created on Aug. 1, 2023, is named 117326000541_Sequence_Listing.xml and is 4,873 bytes in size.

TECHNICAL FIELD

Disclosed herein are methods of reducing collagenase-mediated bruising in a subject having cellulite, methods of treating cellulite in a subject, and collagenase-containing formulations.

BACKGROUND

Collagenases are proteinases that hydrolyze collagen in its native triple helical conformation under physiological conditions. QWO® (CCH-aaes), which is a combination of AUX-I and AUX-II (also referred to as collagenase I and collagenase II), is approved for the treatment of moderate to severe cellulite in the buttocks of adult women. QWO® effectively lyses the subdermal located fibrous septae, the underlying cause of the skin dimpling in women with cellulite, at the site of injection. QWO® has demonstrated an acceptable safety and immunogenicity profile, with injection site bruising being the most common adverse event. Although QWO®-related post-injection bruising generally resolves within 21 days, and before the next treatment session, bruising is bothersome to participants due to the risk of potential skin discoloration and associated swelling and pain.

SUMMARY

Disclosed herein are methods of reducing collagenase-mediated bruising in a subject having cellulite, the methods comprising subcutaneously administering to a treatment area of the subject a total dose of about 0.42 mg of collagenase per treatment session to thereby reduce the collagenase-mediated bruising in the subject.

Disclosed herein are methods of reducing collagenase-mediated bruising in a subject having cellulite, the methods comprising subcutaneously administering to a treatment area of the subject a total dose of about 0.84 mg of collagenase per treatment session, the collagenase having a concentration of about 0.05 mg/ml, to thereby reduce the collagenase-mediated bruising in the subject.

Disclosed herein are methods of reducing collagenase-mediated bruising in a subject having cellulite, the methods comprising subcutaneously administering to a treatment area of the subject a total dose of about 0.84 mg of collagenase per treatment session at a depth of about 0.25 inches to thereby reduce the collagenase-mediated bruising in the subject.

Disclosed herein are methods of reducing collagenase-mediated bruising in a subject having cellulite, the methods comprising subcutaneously administering to a treatment area of the subject a total dose of about 0.84 mg of collagenase per treatment session, the collagenase having a concentration of about 0.09 mg/ml, to thereby reduce the collagenase-mediated bruising in the subject.

Disclosed herein are methods of reducing collagenase-mediated bruising in a subject having cellulite, the methods comprising subcutaneously administering to a treatment area of the subject a composition comprising collagenase, lidocaine, and epinephrine, wherein a total dose of about 0.42 mg of the collagenase is administered per treatment session to thereby reduce the collagenase-mediated bruising in the subject.

Disclosed herein are methods of reducing collagenase-mediated bruising in a subject having cellulite, the methods comprising subcutaneously administering to a treatment area of the subject a total dose of about 0.21 mg of collagenase per treatment session, the collagenase having a concentration of about 0.12 mg/ml, to thereby reduce the collagenase-mediated bruising in the subject.

Disclosed herein are methods of reducing collagenase-mediated bruising in a subject having cellulite, the methods comprising orally administering to the subject tranexamic acid (TXA) and subcutaneously administering to a treatment area of the subject a total dose of about 0.84 mg of collagenase per treatment session to thereby reduce the collagenase-mediated bruising in the subject.

Disclosed herein are methods of reducing bruising and/or skin discoloration associated with collagenase-mediated treatment of cellulite in a subject, the methods comprising subcutaneously administering to a treatment area of the subject a total dose of about 0.42 mg of collagenase per treatment session to thereby reduce the bruising and/or skin discoloration associated with the collagenase-mediated treatment of cellulite in the subject.

Disclosed herein are methods of reducing bruising and/or skin discoloration associated with collagenase-mediated treatment of cellulite in a subject, the methods comprising subcutaneously administering to a treatment area of the subject a total dose of about 0.84 mg of collagenase per treatment session, the collagenase having a concentration of about 0.05 mg/ml, to thereby reduce the bruising and/or skin discoloration associated with the collagenase-mediated treatment of cellulite in the subject.

Disclosed herein are methods of reducing bruising and/or skin discoloration associated with collagenase-mediated treatment of cellulite in a subject, the methods comprising subcutaneously administering to a treatment area of the subject a total dose of about 0.84 mg of collagenase per treatment session at a depth of about 0.25 inches to thereby reduce the bruising and/or skin discoloration associated with the collagenase-mediated treatment of cellulite in the subject.

Disclosed herein are methods of reducing bruising and/or skin discoloration associated with collagenase-mediated treatment of cellulite in a subject, the methods comprising subcutaneously administering to a treatment area of the subject a total dose of about 0.84 mg of collagenase per treatment session, the collagenase having a concentration of about 0.09 mg/ml, to thereby reduce the bruising and/or skin discoloration associated with the collagenase-mediated treatment of cellulite in the subject.

Disclosed herein are methods of reducing bruising and/or skin discoloration associated with collagenase-mediated treatment of cellulite in a subject, the methods comprising subcutaneously administering to a treatment area of the subject a composition comprising collagenase, lidocaine, and epinephrine, wherein a total dose of about 0.42 mg of the collagenase is administered per treatment session to thereby reduce the bruising and/or skin discoloration associated with the collagenase-mediated treatment of cellulite in the subject.

Disclosed herein are methods of reducing bruising and/or skin discoloration associated with collagenase-mediated treatment of cellulite in a subject, the methods comprising subcutaneously administering to a treatment area of the subject a total dose of about 0.21 mg of collagenase per treatment session, the collagenase having a concentration of about 0.12 mg/ml, to thereby reduce the bruising and/or skin discoloration associated with the collagenase-mediated treatment of cellulite in the subject.

Disclosed herein are methods of reducing bruising and/or skin discoloration associated with collagenase-mediated treatment of cellulite in a subject, the methods comprising orally administering to the subject tranexamic acid and subcutaneously administering to a treatment area of the subject a total dose of about 0.84 mg of collagenase per treatment session to thereby reduce the bruising and/or skin discoloration associated with the collagenase-mediated treatment of cellulite in the subject.

Also provided are methods of treating cellulite in a subject, the methods comprising subcutaneously administering to a treatment area of the subject a total dose of about 0.42 mg of collagenase per treatment session to thereby treat the cellulite in the subject.

Disclosed herein are methods of treating cellulite in a subject, the methods comprising subcutaneously administering to a treatment area of the subject a total dose of about 0.84 mg of collagenase per treatment session, the collagenase having a concentration of about 0.05 mg/ml, to thereby treat the cellulite in the subject.

Disclosed herein are methods of treating cellulite in a subject, the methods comprising subcutaneously administering to a treatment area of the subject a total dose of about 0.84 mg of collagenase per treatment session, the collagenase having a concentration of about 0.23 mg/ml, at a depth of about 0.25 inches to thereby treat the cellulite in the subject.

Disclosed herein are methods of treating cellulite in a subject, the methods comprising subcutaneously administering to a treatment area of the subject a total dose of about 0.84 mg of collagenase per treatment session, the collagenase having a concentration of about 0.09 mg/ml, to thereby treat the cellulite in the subject.

Disclosed herein are methods of treating cellulite in a subject, the methods comprising subcutaneously administering to a treatment area of the subject a composition comprising collagenase, lidocaine, and epinephrine, wherein a total dose of about 0.42 mg of the collagenase is administered per treatment session to thereby treat the cellulite in the subject.

Disclosed herein are methods of treating cellulite in a subject, the methods comprising subcutaneously administering to a treatment area of the subject a total dose of about 0.21 mg of collagenase per treatment session, the collagenase having a concentration of about 0.12 mg/ml, to thereby treat the cellulite in the subject.

Also provided herein are formulations comprising a collagenase, lidocaine, and epinephrine.

BRIEF DESCRIPTION OF THE DRAWINGS

The summary, as well as the following detailed description, is further understood when read in conjunction with the appended drawings. For the purpose of illustrating the disclosed methods and formulations, there are shown in the drawings exemplary embodiments of the methods and formulations; however, the methods and formulations are not limited to the specific embodiments disclosed. In the drawings:

FIG. 2 illustrates an exemplary Investigator Assessment of Bruising Severity Scale (IABSS) used to rate the severity of bruising and/or skin discoloration following the subcutaneous administration of collagenase to a treatment area (in this embodiment, the buttocks).

DETAILED DESCRIPTION OF ILLUSTRATIVE EMBODIMENTS

Figure 1:
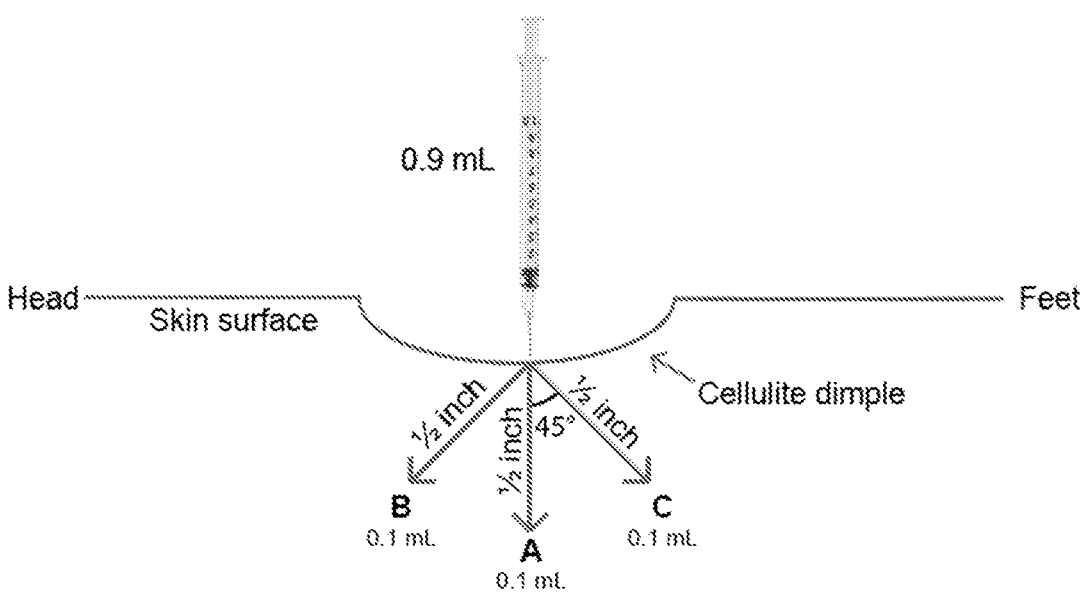
FIG. 1 illustrates an exemplary "three-injection technique" (also referred to as a "three-aliquot" technique) in which subcutaneous injections are administered as three 0.1-mL aliquots (total injection volume of 0.3 ml), with 1 aliquot administered perpendicular to the skin (A) and the other 2 aliquots administered at a 45-degree angle superior (B) or inferior (C) to the perpendicular axis. The depth of the injection in FIG. 1 is 0.5 inches, but injection depths of 0.25 inches can also be used. Each syringe contains 0.9 mL to allow for 3 injections per syringe, with a maximum of 12 injections per treatment area.

The disclosed methods and formulations may be understood more readily by reference to the following detailed description taken in connection with the accompanying figures, which form a part of this disclosure. It is to be understood that the disclosed methods and formulations are not limited to the specific methods and formulations described and/or shown herein, and that the terminology used herein is for the purpose of describing particular embodiments by way of example only and is not intended to be limiting of the claimed methods and formulations.

Unless specifically stated otherwise, any description as to a possible mechanism or mode of action or reason for improvement is meant to be illustrative only, and the disclosed methods and formulations are not to be constrained by the correctness or incorrectness of any such suggested mechanism or mode of action or reason for improvement.

Where a range of numerical values is recited or established herein, the range includes the endpoints thereof and all the individual integers and fractions within the range, and also includes each of the narrower ranges therein formed by all the various possible combinations of those endpoints and internal integers and fractions to form subgroups of the larger group of values within the stated range to the same extent as if each of those narrower ranges was explicitly recited. Where a range of numerical values is stated herein as being greater than a stated value, the range is nevertheless finite and is bounded on its upper end by a value that is operable within the context of the herein disclosure. Where a range of numerical values is stated herein as being less than a stated value, the range is nevertheless bounded on its lower end by a non-zero value. It is not intended that the scope of the methods and formulations be limited to the specific values recited when defining a range. All ranges are inclusive and combinable.

It is to be appreciated that certain features of the disclosed methods and formulations which are, for clarity, described herein in the context of separate embodiments, may also be provided in combination in a single embodiment. Conversely, various features of the disclosed methods and formulations that are, for brevity, described in the context of a single embodiment, may also be provided separately or in any subcombination.

As used herein, the singular forms "a," "an." and "the" include the plural.

Various terms relating to aspects of the description are used throughout the specification and claims. Such terms are to be given their ordinary meaning in the art unless otherwise indicated. Other specifically defined terms are to be construed in a manner consistent with the definitions provided herein.

The term "about" when used in reference to numerical ranges, cutoffs, or specific values is used to indicate that the recited values may vary by up to as much as 15% from the listed value. Thus, the term "about" is used to encompass variations of ±15% or less, variations of ±10% or less, variations of ±5% or less, variations of ±1% or less, variations of ±0.5% or less, or variations of ±0.1% or less from the specified value. When values are expressed as approximations, by use of the antecedent "about." it will be understood that the particular value forms another embodiment. Reference to a particular numerical value includes at least that particular value, unless the context clearly dictates otherwise.

The term "comprising" is intended to include examples encompassed by the terms "consisting essentially of" and "consisting of"; similarly, the term "consisting essentially of" is intended to include examples encompassed by the term "consisting of."

The term "subject" as used herein is intended to mean any animal, in particular, mammals. Thus, the methods are applicable to human and nonhuman animals, although most preferably with humans. "Subject" and "patient" are used interchangeably herein.

As used herein. "administering" and similar terms indicate a procedure by which the collagenase or composition/pharmaceutical formulation comprising the collagenase is injected into a subject such that target cells, tissues, or segments of the body of the subject are contacted with the collagenase.

As used herein, "collagenase-mediated bruising" refers to at least one of bruising, hematoma, hemorrhaging, ecchymosis, and discoloration that occurs at and/or around the injection site following the administration of collagenase.

"Treat," "treatment," and like terms include reducing and/or eliminating the cellulite, reducing and/or eliminating the underlying cause of the cellulite, reducing and/or eliminating the likelihood of cellulite, and inducing and/or improving the overall cosmetic qualities of the skin.

As used herein, "reducing bruising" and like phrases refers to an at least 1 level improvement on the Investigator Assessment of Bruising Severity Scale (IABSS).

The term "treatment area" refers to an area of the subject that has the cellulite and to which the specified total dose of collagenase is administered. Exemplary treatment areas include, for example, the left buttock, the right buttock, or both the eft and right buttocks.

The term "treatment session" is synonymous with "treatment visit" and includes a single visit to a doctor's office in which the collagenase or formulations/compositions comprising the collagenase is administered, or a single self-administration period if the subject is self-administering the collagenase or formulations/compositions comprising the collagenase. A treatment session or visit may involve treating a single treatment area or treating multiple treatment areas. For example, in the case of the buttocks, a treatment session may involve administering the specified total dose of collagenase to each of the left and right buttocks. Alternatively, a treatment session or visit may involve administering the specified total dose of collagenase to the left buttock only.

The term "total dose" refers to the total amount of collagenase administered to a treatment area in a given treatment session. For example, in the herein disclosed examples, the total dose per treatment session refers to the total dose of collagenase administered to a single buttock per treatment session.

Methods of Reducing Collagenase-Mediated Bruising in a Subject Having Cellulite

Disclosed herein are methods of reducing collagenase-mediated bruising in a subject having cellulite. The methods can comprise subcutaneously administering to a treatment area of the subject a total dose of about 0.42 mg of collagenase per treatment session to thereby reduce the collagenase-mediated bruising in the subject. In some embodiments, the collagenase can be administered using a three-injection technique (as described herein). In some embodiments, the collagenase can be administered at a depth of about 0.5 inches. Thus, the methods can comprise subcutaneously administering to a treatment area of the subject a total dose of about 0.42 mg of collagenase per treatment session using a three-injection technique at a depth of about 0.5 inches to thereby reduce the collagenase-mediated bruising in the subject. In some embodiments, the collagenase can have a concentration of about 0.23 mg/ml. In some embodiments, the subject can receive more than one treatment session, wherein the treatment sessions are about 3 weeks apart. In some embodiments, the subject can receive more than one treatment session, wherein the treatment sessions are about 42 days apart. The bruising can be reduced compared to a level of bruising associated with administering QWO® according to its U.S. prescribing information (www_accessdata.fda.gov/drugsatfda_docs/label/2020/761146s000lbl.pdf; see also Example 2 herein). In some embodiments, the bruising can be reduced compared to a level of bruising associated with subcutaneously administering to the treatment area of the subject a total dose of about 0.84 mg of collagenase per treatment session using the three-injection technique at a depth of 0.5 inches. In some embodiments, the bruising can be reduced compared to a level of bruising associated with subcutaneously administering to the treatment area of the subject a total dose of about 0.84 mg of collagenase per treatment session, the collagenase having a concentration of about 0.23 mg/ml, using the three-injection technique at a depth of 0.5 inches.

The methods of reducing collagenase-mediated bruising in a subject having cellulite can comprise subcutaneously administering to a treatment area of the subject a total dose of about 0.84 mg of collagenase per treatment session, the collagenase having a concentration of about 0.05 mg/ml, to thereby reduce the collagenase-mediated bruising in the subject. In some embodiments, the collagenase can be administered using a three-injection technique. In some embodiments, the collagenase can be administered at a depth of about 0.5 inches. Thus, the methods of reducing collagenase-mediated bruising in a subject having cellulite can comprise subcutaneously administering to a treatment area of the subject a total dose of about 0.84 mg of collagenase per treatment session, the collagenase having a concentration of about 0.05 mg/ml, using a three-injection technique at a depth of about 0.5 inches to thereby reduce the collagenase-mediated bruising in the subject. In some embodiments, the subject can receive more than one treatment session, wherein the treatment sessions are about 3 weeks apart. The bruising can be reduced compared to a level of bruising associated with administering QWO® according to its U.S. prescribing information. In some embodiments, the bruising can be reduced compared to a level of bruising associated with subcutaneously administering to the treatment area of the subject a total dose of about 0.84 mg of collagenase per treatment session, the collagenase having a concentration of about 0.23 mg/ml, using the three-injection technique at a depth of about 0.5 inches.

The methods of reducing collagenase-mediated bruising in a subject having cellulite can comprise subcutaneously administering to a treatment area of the subject a total dose of about 0.84 mg of collagenase per treatment session at a depth of about 0.25 inches to thereby reduce the collagenase-mediated bruising in the subject. In some embodiments, the collagenase can be administered using a three-injection technique. Thus, the methods of reducing collagenase-mediated bruising in a subject having cellulite can comprise subcutaneously administering to a treatment area of the subject a total dose of about 0.84 mg of collagenase per treatment session using a three-injection technique at a depth of about 0.25 inches to thereby reduce the collagenase-mediated bruising in the subject. In some embodiments, the collagenase can have a concentration of about 0.23 mg/ml. In some embodiments, the subject can receive more than one treatment session, wherein the treatment sessions are about 3 weeks apart. The bruising can be reduced compared to a level of bruising associated with administering QWO® according to its U.S. prescribing information. In some embodiments, the bruising can be reduced compared to a level of bruising associated with subcutaneously administering to the treatment area of the subject a total dose of about 0.84 mg of collagenase per treatment session using the three-injection technique at a depth of about 0.5 inches. In some embodiments, the bruising can be reduced compared to a level of bruising associated with subcutaneously administering to the treatment area of the subject a total dose of about 0.84 mg of collagenase per treatment session, the collagenase having a concentration of about 0.23 mg/ml, using the three-injection technique at a depth of about 0.5 inches.

An exemplary three-injection technique is illustrated in FIG. 1. As shown in that Figure, subcutaneous injections can be administered as three 0.1-mL aliquots (total injection volume of 0.3 mL), with 1 aliquot administered perpendicular to the skin (A) and the other 2 aliquots administered at a 45-degree angle superior (8) or inferior (C) to the perpendicular axis. The depth of the injection in FIG. 1 is 0.5 inches, but other injection depths, such as 0.25 inches, can also be used. Each syringe can contain 0.9 ml, to allow for 3 injections per syringe, with a maximum of 12 injections per treatment area.

The volume of each aliquot injected depends, in part, on the severity of the cellulite being treated and the size of the treatment area. The total volume to be injected can be divided evenly in each aliquot. For example, if 0.3 ml of the pharmaceutical formulation are to be injected, each of three aliquots can contain 0.1 ml. Suitable volumes of each aliquot include, for example, about 0.05 ml, about 0.075 ml, about 0.1 ml, about 0.2 ml, about 0.3 ml, about 0.4 ml, about 0.5 ml, about 0.6 ml, about 0.7 ml, about 0.8 ml, about 0.9 ml, or about 1.0 ml. In some embodiments, each aliquot has a volume of about 0.05 ml to about 0.5 ml.

The methods of reducing collagenase-mediated bruising in a subject having cellulite can comprise subcutaneously administering to a treatment area of the subject a total dose of about 0.84 mg of collagenase per treatment session, the collagenase having a concentration of about 0.09 mg/ml, to thereby reduce the collagenase-mediated bruising in the subject. In some embodiments, the collagenase can be administered using a single aliquot injection. In some embodiments, the collagenase can be administered at a depth of about 0.25 inches. Thus, the methods of reducing collagenase-mediated bruising in a subject having cellulite can comprise subcutaneously administering to a treatment area of the subject a total dose of about 0.84 mg of collagenase per treatment session, the collagenase having a concentration of about 0.09 mg/ml, using a single aliquot injection at a depth of about 0.25 inches to thereby reduce the collagenase-mediated bruising in the subject. In some embodiments, the administering comprises up to 30 single aliquot injections of the collagenase to the treatment area per treatment session. In some embodiments, the administering comprises greater than 30 single aliquot injections of the collagenase to the treatment area per treatment session. In some embodiments, the subject can receive more than one treatment session, wherein the treatment sessions are about 3 weeks apart. The bruising can be reduced compared to a level of bruising associated with administering QWO® according to its U.S. prescribing information. In some embodiments, the bruising can be reduced compared to a level of bruising associated with subcutaneously administering to the treatment area of the subject a total dose of about 0.84 mg of collagenase per treatment session, the collagenase having a concentration of about 0.23 mg/ml, using the single aliquot injection at a depth of about 0.25 inches. In some embodiments the administering comprises up to 12 single aliquot injections of the collagenase to the treatment area per treatment session. In some embodiments the administering comprises greater than 12 single aliquot injections of the collagenase to the treatment area per treatment session.

The number of injections administered via the single aliquot injection in a single treatment session is based, in part, on the severity of the cellulite and the size of the treatment area. One, two, three, four, five, six, seven, eight, nine, ten, 11, 12, 13, 14, 15, 16, 17, 18, 19, 20, 25, 30, 35, 40, 45, 50, 55, 60, 65, 70, 75, 80, 85, 90, 95, 100, or greater than 100 injections can be administered to the treatment area in a single treatment session.

When multiple injections are administered in a single treatment session, the injections can be evenly, or approximately evenly, spaced apart. The spacing between injections depends, in part, on the volume injected and the size of the treatment area. The injections, for example, can be about 0.25 cm, about 0.5 cm, about 0.75 cm, about 1.0 cm, about 1.25 cm, about 1.5 cm, about 1.75 cm, about 2.0 cm, about 2.25 cm, about 2.5 cm, about 2.75 cm, about 3.0 cm, about 3.25 cm, about 3.5 cm, about 3.75 cm, about 4.0 cm, or more than 4.0 cm apart. In some embodiments, the injections are spaced about 2 cm to about 3 cm apart.

Figure 3:
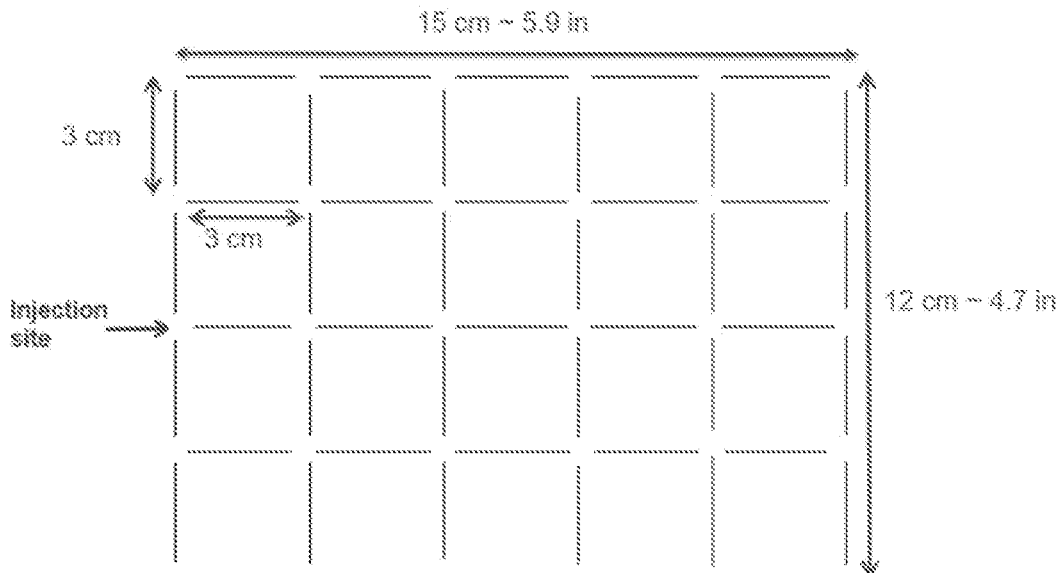
FIG. 3 illustrates an exemplary Grid injection pattern in which up to 30 injections can be administered to a treatment area, wherein each injection is spaced approximately 3 cm apart.

When multiple injections are administered in a single treatment session, the injections can be administered at random sites within the treatment area, as one or more patterns within the treatment area, or at random sites and as one or more patterns within the treatment area. In some embodiments, the injections are spaced in a grid pattern. An exemplary grid pattern is shown in FIG. 3. Grid pattern, as used herein, refers to a reproducible injection pattern wherein the injections are evenly spaced. The grid pattern can be hexagonal, circular, square, rectangular, triangular, to name a few. In some embodiments, the injections in the grid pattern are spaced about 2 cm to about 3 cm apart. When injecting the collagenase or pharmaceutical formulations/ compositions comprising the collagenase at random sites, as one or more patterns, or at random sites and as one or more patterns, the injections can comprise a single aliquot or multiple aliquots of the pharmaceutical formulation to each site within the treatment area.

Suitable volumes of each injection within the grid pattern include, for example, about 0.1 ml, about 0.2 ml, about 0.3 ml, about 0.4 ml, about 0.5 ml, about 0.6 ml, about 0.7 ml, about 0.8 ml, about 0.9 ml, or about 1.0 ml. In some embodiments, each injection has a volume of about 0.1 ml to 0.3 ml.

The collagenase in any of the herein disclosed methods of reducing collagenase-mediated bruising can be a component of a composition/pharmaceutical formulation. In some embodiments, the collagenase can be a component of a composition/pharmaceutical formulation comprising the collagenase, mannitol, sucrose, and tromethamine. The composition/pharmaceutical formulation can further comprise HCl to adjust the pH as needed. The composition/ pharmaceutical formulation can have a pH of approximately 8.0.

The methods of reducing collagenase-mediated bruising in a subject having cellulite can comprise subcutaneously administering to a treatment area of the subject a composition comprising collagenase, lidocaine, and epinephrine, wherein a total dose of about 0.42 mg of the collagenase is administered per treatment session to thereby reduce the collagenase-mediated bruising in the subject. In some embodiments, the collagenase can be administered using a three-injection technique. In some embodiments, the collagenase can be administered at a depth of about 0.5 inches. Thus, the methods of reducing collagenase-mediated bruising in a subject having cellulite can comprise subcutaneously administering to a treatment area of the subject a composition comprising collagenase, lidocaine, and epinephrine, wherein a total dose of about 0.42 mg of the collagenase is administered per treatment session using a three-injection technique at a depth of about 0.5 inches to thereby reduce the collagenase-mediated bruising in the subject. The collagenase can have a concentration of about 0.23 mg/ml. The lidocaine can have a concentration of about 5 mg/mL, about 10 mg/mL, about 15 mg/mL, or about 20 mg/mL. The epinephrine can have a concentration of about 5 mcg/mL or about 10 mcg/mL. In some embodiments, the composition can comprise about 0.23 mg/ml collagenase, 2% lidocaine (20 mg/ml), and 1:200,000 epinephrine (5 mgc/ml). In some embodiments, the composition further comprises mannitol, sucrose, and tromethamine. Thus, the methods can comprise subcutaneously administering to a treatment area of the subject a composition comprising collagenase, lidocaine, epinephrine, mannitol, sucrose, and tromethamine, wherein a total dose of about 0.42 mg of the collagenase is administered per treatment session to thereby reduce the collagenase-mediated bruising in the subject. In some embodiments, the subject can receive more than one treatment session, wherein the treatment sessions are about 3 weeks apart. The bruising can be reduced compared to a level of bruising associated with administering QWO® according to its U.S. prescribing information. In some embodiments, the bruising can be reduced compared to a level of bruising associated with subcutaneously adminis-tering to the treatment area of the subject a composition comprising the collagenase, wherein a total dose of about 0.84 mg of the collagenase is administered per treatment session using a three-injection technique at a depth of about 0.5 inches. In some embodiments, the bruising can be reduced compared to a level of bruising associated with subcutaneously administering to the treatment area of the subject a composition comprising about 0.23 mg/ml of the collagenase, wherein a total dose of about 0.84 mg of the collagenase is administered per treatment session using a three-injection technique at a depth of about 0.5 inches. In some embodiments, the bruising is reduced compared to a level of bruising associated with subcutaneously adminis-tering to the treatment area of the subject a composition comprising the collagenase, mannitol, sucrose, and trometh-amine, wherein a total dose of about 0.84 mg of the collagenase is administered per treatment session using a three-injection technique at a depth of about 0.5 inches.

The methods of reducing collagenase-mediated bruising in a subject having cellulite can comprise subcutaneously administering to a treatment area of the subject a total dose of about 0.21 mg of collagenase per treatment session, the collagenase having a concentration of about 0.12 mg/ml, to thereby reduce the collagenase-mediated bruising in the subject. In some embodiments, the collagenase can be administered using a three-injection technique. In some embodiments, the collagenase can be administered at a depth of about 0.5 inches. Thus, the methods of reducing collagenase-mediated bruising in a subject having cellulite can comprise subcutaneously administering to a treatment area of the subject a total dose of about 0.21 mg of collagenase per treatment session, the collagenase having a concentration of about 0.12 mg/ml, using a three-injection technique at a depth of about 0.5 inches to thereby reduce the collagenase-mediated bruising in the subject. In some embodiments, the subject can receive more than one treat-ment session, wherein the treatment sessions are about 42 days apart. The bruising can be reduced compared to a level of bruising associated with administering QWO® according to its U.S. prescribing information. In some embodiments, the bruising can be reduced compared to a level of bruising associated with subcutaneously administering to the treat-ment area of the subject a total dose of about 0.42 mg of collagenase per treatment session using the three-injection technique at a depth of about 0.5 inches. In some embodi-ments, the bruising can be reduced compared to a level of bruising associated with subcutaneously administering to the treatment area of the subject a total dose of about 0.42 mg of collagenase per treatment session, the collagenase having a concentration of about 0.23 mg/ml, using the three-injection technique at a depth of about 0.5 inches, wherein the subject received more than one treatment ses-sions that are about 42 days apart.

The methods of reducing collagenase-mediated bruising in a subject having cellulite can comprise orally administering to the subject tranexamic acid and subcutaneously administering to a treatment area of the subject a total dose of about 0.84 mg of collagenase per treatment session to thereby reduce the collagenase-mediated bruising in the subject. In some embodiments, the tranexamic acid has a concentration of about 500 mg to about 1500 mg. In some embodiments, the tranexamic acid has a concentration of about 1300 mg. Thus, the methods of reducing collagenase-mediated bruising in a subject having cellulite can comprise orally administering to the subject about 1300 mg of tranexamic acid and subcutaneously administering to a treatment area of the subject a total dose of about 0.84 mg of collagenase per treatment session to thereby reduce the collagenase-mediated bruising in the subject. In some embodiments, the collagenase can be administered using a three-injection technique. In some embodiments, the collagenase can be administered at a depth of about 0.5 inches. The methods of reducing collagenase-mediated bruising in a subject having cellulite can comprise orally administering to the subject about 1300 mg of tranexamic acid and subcutaneously administering to a treatment area of the subject a total dose of about 0.84 mg of collagenase per treatment session using a three-injection technique at a depth of about 0.5 inches to thereby reduce the collagenase-mediated bruising in the subject. In some embodiments, the collagenase can have a concentration of about 0.23 mg/ml. In some embodiments, the subject can receive more than one treatment session, wherein the treatment sessions are about 3 weeks apart. In some embodiments, the tranexamic acid is orally administered three times a day for five days during the first treatment session. In some aspects, during the first treatment session, the tranexamic acid is orally administered to the subject three times on the day before the administering of the collagenase, three times on the day of the administering of the collagenase, and on each of days 2, 3, and 4 after the administering of the collagenase. In some embodiments, the tranexamic acid is orally administered three times a day for five days during the second treatment session. In some aspects, during the second treatment session, the tranexamic acid is orally administered to the subject three times on the day before the administering of the collagenase, three times on the day of the administering of the collagenase, and on each of days 2, 3, and 4 after the administering of the collagenase. The bruising can be reduced compared to a level of bruising associated with administering QWO® according to its U.S. prescribing information. In some embodiments, the collagenase-mediated bruising is reduced compared to a level of collagenase-mediated bruising associated with subcutaneously administering to the treatment area of the subject a total dose of about 0.84 mg of collagenase per treatment session using the three-injection technique at a depth of 0.5 inches.

The level of bruising can be evaluated using an Investigator Assessment of Bruising Severity Scale (IABSS). An exemplary IABSS is illustrated in FIG. 2. As shown in FIG. 2, the exemplary IABSS contains 5 images showing bruising in a treatment area (left and right buttocks) of one or more example subjects, the treatment area in each of the 5 images of the example subjects corresponding to the location of the treatment area of the subject to which the collagenase is administered, wherein each of the 5 images has a different bruising severity rating comprising a numerical value and description. The exemplary IABSS contains the following severity ratings:

0—none or almost none: no bruising or almost no bruising observed;

1—mild: mild intensity bruising, pink-light red color covering approximately 25% of the buttock;

2—moderate: moderate intensity bruising, deep red to purple color covering approximately 50% of the buttock;

3—severe: severe bruising, deep purple color covering approximately 75% of the buttock; and 4—very severe: severe bruising, deep to darkest purple color covering approximately 100% of the buttock.

A reduction in the level of bruising can include an at least one-point improvement (i.e., lowering) on the IABSS. Suitable reductions include, for example, a severity rating of 4 to 3, a severity rating of 3 to 2, a severity rating of 2 to 1, a severity rating of 1 to 0, a severity rating of 4 to 2, a severity rating of 4 to 1, a severity rating of 4 to 0, and so on.

Methods of Reducing Bruising and/or Skin Discoloration Associated with Collagenase-Mediated Treatment of Cellulite in a Subject Disclosed herein are methods of reducing bruising and/or skin discoloration associated with collagenase-mediated treatment of cellulite in a subject. The methods can comprise subcutaneously administering to a treatment area of the subject a total dose of about 0.42 mg of collagenase per treatment session to thereby reduce the bruising and/or skin discoloration associated with the collagenase-mediated treatment of cellulite in the subject. In some embodiments, the collagenase can be administered using a three-injection technique. In some embodiments, the collagenase can be administered at a depth of about 0.5 inches. Thus, the methods can comprise subcutaneously administering to a treatment area of the subject a total dose of about 0.42 mg of collagenase per treatment session using a three-injection technique at a depth of about 0.5 inches to thereby reduce the bruising and/or skin discoloration associated with the collagenase-mediated treatment of cellulite in the subject. In some embodiments, the collagenase can have a concentration of about 0.23 mg/ml. In some embodiments, the subject can receive more than one treatment session, wherein the treatment sessions are about 3 weeks apart. In some embodiments, the subject can receive more than one treatment session, wherein the treatment sessions are about 42 days apart. The bruising and/or skin discoloration can be reduced compared to a level of bruising and/or skin discoloration associated with administering QWO® according to its U.S. prescribing information. In some embodiments, the bruising and/or skin discoloration can be reduced compared to a level of bruising and/or skin discoloration associated with subcutaneously administering to the treatment area of the subject a total dose of about 0.84 mg of collagenase per treatment session using the three-injection technique at a depth of 0.5 inches. In some embodiments, the bruising and/or skin discoloration can be reduced compared to a level of bruising and/or skin discoloration associated with subcutaneously administering to the treatment area of the subject a total dose of about 0.84 mg of collagenase per treatment session, the collagenase having a concentration of about 0.23 mg/ml, using the three-injection technique at a depth of 0.5 inches.

The methods of reducing bruising and/or skin discoloration associated with collagenase-mediated treatment of cellulite in a subject can comprise subcutaneously administering to a treatment area of the subject a total dose of about 0.84 mg of collagenase per treatment session, the collagenase having a concentration of about 0.05 mg/ml, to thereby reduce the bruising and/or skin discoloration associated with the collagenase-mediated treatment of cellulite in the subject. In some embodiments, the collagenase can be administered using a three-injection technique. In some embodiments, the collagenase can be administered at a depth of about 0.5 inches. Thus, the methods of reducing bruising and/or skin discoloration associated with collagenase-mediated treatment of cellulite in a subject can comprise subcutaneously administering to a treatment area of the subject a total dose of about 0.84 mg of collagenase per treatment session, the collagenase having a concentration of about 0.05 mg/ml, using a three-injection technique at a depth of about 0.5 inches to thereby reduce the bruising and/or skin discoloration associated with the collagenase-mediated treatment of cellulite in the subject. In some embodiments, the subject can receive more than one treatment session, wherein the treatment sessions are about 3 weeks apart. The bruising and/or skin discoloration can be reduced compared to a level of bruising and/or skin discoloration associated with administering QWO® according to its U.S. prescribing information. In some embodiments, the bruising and/or skin discoloration can be reduced compared to a level of bruising and/or skin discoloration associated with subcutaneously administering to the treatment area of the subject a total dose of about 0.84 mg of collagenase per treatment session, the collagenase having a concentration of about 0.23 mg/ml, using the three-injection technique at a depth of about 0.5 inches.

The methods of reducing bruising and/or skin discoloration associated with collagenase-mediated treatment of cellulite in a subject can comprise subcutaneously administering to a treatment area of the subject a total dose of about 0.84 mg of collagenase per treatment session at a depth of about 0.25 inches to thereby reduce the bruising and/or skin discoloration associated with the collagenase-mediated treatment of cellulite in the subject. In some embodiments, the collagenase can be administered using a three-injection technique. Thus, the methods of reducing bruising and/or skin discoloration associated with collagenase-mediated treatment of cellulite in a subject can comprise subcutaneously administering to a treatment area of the subject a total dose of about 0.84 mg of collagenase per treatment session using a three-injection technique at a depth of about 0.25 inches to thereby reduce the bruising and/or skin discoloration associated with the collagenase-mediated treatment of cellulite in the subject. In some embodiments, the collagenase can have a concentration of about 0.23 mg/ml. In some embodiments, the subject can receive more than one treatment session, wherein the treatment sessions are about 3 weeks apart. The bruising and/or skin discoloration can be reduced compared to a level of bruising and/or skin discoloration associated with administering QWO® according to its U.S. prescribing information. In some embodiments, the bruising and/or skin discoloration can be reduced compared to a level of bruising and/or skin discoloration associated with subcutaneously administering to the treatment area of the subject a total dose of about 0.84 mg of collagenase per treatment session using the three-injection technique at a depth of about 0.5 inches. In some embodiments, the bruising and/or skin discoloration can be reduced compared to a level of bruising and/or skin discoloration associated with subcutaneously administering to the treatment area of the subject a total dose of about 0.84 mg of collagenase per treatment session, the collagenase having a concentration of about 0.23 mg/ml, using the three-injection technique at a depth of about 0.5 inches.

The volume of each aliquot injected depends, in part, on the severity of the cellulite being treated and the size of the treatment area. The total volume to be injected can be divided evenly in each aliquot. For example, if 0.3 ml of the pharmaceutical formulation are to be injected, each of three aliquots can contain 0.1 ml. Suitable volumes of each aliquot include, for example, about 0.05 ml, about 0.075 ml, about 0.1 ml, about 0.2 ml, about 0.3 ml, about 0.4 ml, about 0.5 ml, about 0.6 ml, about 0.7 ml, about 0.8 ml, about 0.9 ml, or about 1.0 ml. In some embodiments, each aliquot has a volume of about 0.05 ml to about 0.5 ml.

The methods of reducing bruising and/or skin discoloration associated with collagenase-mediated treatment of cellulite in a subject can comprise subcutaneously administering to a treatment area of the subject a total dose of about 0.84 mg of collagenase per treatment session, the collagenase having a concentration of about 0.09 mg/ml, to thereby reduce the bruising and/or skin discoloration associated with the collagenase-mediated treatment of cellulite in the subject. In some embodiments, the collagenase can be administered using a single aliquot injection. In some embodiments, the collagenase can be administered at a depth of about 0.25 inches. Thus, the methods of reducing bruising and/or skin discoloration associated with collagenase-mediated treatment of cellulite in a subject can comprise subcutaneously administering to a treatment area of the subject a total dose of about 0.84 mg of collagenase per treatment session, the collagenase having a concentration of about 0.09 mg/ml, using a single aliquot injection at a depth of about 0.25 inches to thereby reduce the bruising and/or skin discoloration associated with the collagenase-mediated treatment of cellulite in the subject. In some embodiments, the administering comprises up to 30 single aliquot injections of the collagenase to the treatment area per treatment session. In some embodiments, the administering comprises greater than 30 single aliquot injections of the collagenase to the treatment area per treatment session. In some embodiments, the subject can receive more than one treatment session, wherein the treatment sessions are about 3 weeks apart. The bruising and/or skin discoloration can be reduced compared to a level of bruising and/or skin discoloration associated with administering QWO® according to its U.S. prescribing information. In some embodiments, the bruising and/or skin discoloration can be reduced compared to a level of bruising and/or skin discoloration associated with subcutaneously administering to the treatment area of the subject a total dose of about 0.84 mg of collagenase per treatment session, the collagenase having a concentration of about 0.23 mg/ml, using the single aliquot injection at a depth of about 0.25 inches. In some embodiments the administering comprises up to 12 single aliquot injections of the collagenase to the treatment area per treatment session. In some embodiments the administering comprises greater than 12 single aliquot injections of the collagenase to the treatment area per treatment session.

The number of injections administered via the single aliquot injection in a single treatment session is based, in part, on the severity of the cellulite and the size of the treatment area. One, two, three, four, five, six, seven, eight, nine, ten, II, 12, 13, 14, 15, 16, 17, 18, 19, 20, 25, 30, 35, 40, 45, 50, 55, 60, 65, 70, 75, 80, 85, 90, 95, 100, or greater than 100 injections can be administered to the treatment area in a single treatment session.

When multiple injections are administered in a single treatment session, the injections can be evenly, or approximately evenly, spaced apart. The spacing between injections depends, in part, on the volume injected and the size of the treatment area. The injections, for example, can be about 0.25 cm, about 0.5 cm, about 0.75 cm, about 1.0 cm, about 1.25 cm, about 1.5 cm, about 1.75 cm, about 2.0 cm, about 2.25 cm, about 2.5 cm, about 2.75 cm, about 3.0 cm, about 3.25 cm, about 3.5 cm, about 3.75 cm, about 4.0 cm, or more than 4.0 cm apart. In some embodiments, the injections are spaced about 2 cm to about 3 cm apart.

When multiple injections are administered in a single treatment session, the injections can be administered at random sites within the treatment area, as one or more patterns within the treatment area, or at random sites and as one or more patterns within the treatment area. In some embodiments, the injections are spaced in a grid pattern. In some embodiments, the injections in the grid pattern are spaced about 2 cm to about 3 cm apart. When injecting the collagenase or pharmaceutical formulations/compositions comprising the collagenase at random sites, as one or more patterns, or at random sites and as one or more patterns, the injections can comprise a single aliquot or multiple aliquots of the pharmaceutical formulation to each site within the treatment area.

Suitable volumes of each injection within the grid pattern include, for example, about 0.1 ml, about 0.2 ml, about 0.3 ml, about 0.4 ml, about 0.5 ml, about 0.6 ml, about 0.7 ml, about 0.8 ml, about 0.9 ml, or about 1.0 ml. In some embodiments, each injection has a volume of about 0.1 ml to 0.3 ml.

The collagenase in any of the herein disclosed methods of reducing bruising and/or skin discoloration can be a component of a composition/pharmaceutical formulation. In some embodiments, the collagenase can be a component of a composition/pharmaceutical formulation comprising the collagenase, mannitol, sucrose, and tromethamine. The composition/pharmaceutical formulation can further comprise HCl to adjust the pH as needed. The composition/pharmaceutical formulation can have a pH of approximately 8.0.

The methods of reducing bruising and/or skin discoloration associated with collagenase-mediated treatment of cellulite in a subject can comprise subcutaneously administering to a treatment area of the subject a composition comprising collagenase, lidocaine, and epinephrine, wherein a total dose of about 0.42 mg of the collagenase is administered per treatment session to thereby reduce the bruising and/or skin discoloration associated with the collagenase-mediated treatment of cellulite in the subject. In some embodiments, the collagenase can be administered using a three-injection technique. In some embodiments, the collagenase can be administered at a depth of about 0.5 inches. Thus, the methods of reducing bruising and/or skin discoloration associated with collagenase-mediated treatment of cellulite in a subject can comprise subcutaneously administering to a treatment area of the subject a composition comprising collagenase, lidocaine, and epinephrine, wherein a total dose of about 0.42 mg of the collagenase is administered per treatment session using a three-injection technique at a depth of about 0.5 inches to thereby reduce the bruising and/or skin discoloration associated with the collagenase-mediated treatment of cellulite in the subject. The collagenase can have a concentration of about 0.23 mg/mL. The lidocaine can have a concentration of about 5 mg/mL, about 10 mg/mL, about 15 mg/mL, or about 20 mg/mL. The epinephrine can have a concentration of about 5 mcg/mL or about 10 mcg/mL. In some embodiments, the composition can comprise about 0.23 mg/ml collagenase, 2% lidocaine (20 mg/ml), and 1:200,000 epinephrine (5 mgc/ml). In some embodiments, the composition further comprises mannitol, sucrose and tromethamine. Thus, the methods can comprise subcutaneously administering to a treatment area of the subject a composition comprising collagenase, lidocaine, epinephrine, mannitol, sucrose, and tromethamine, wherein a total dose of about 0.42 mg of the collagenase is administered per treatment session using a three-injection technique at a depth of about 0.5 inches to thereby reduce the bruising and/or skin discoloration associated with the collagenase-mediated treatment of cellulite in the subject. In some embodiments, the subject can receive more than one treatment session, wherein the treatment sessions are about 3 weeks apart. The bruising and/or skin discoloration can be reduced compared to a level of bruising and/or skin discoloration associated with administering QWO® according to its U.S. prescribing information. In some embodiments, the bruising and/or skin discoloration can be reduced compared to a level of bruising and/or skin discoloration associated with subcutaneously administering to the treatment area of the subject a composition comprising the collagenase, wherein a total dose of about 0.84 mg of the collagenase is administered per treatment session using a three-injection technique at a depth of about 0.5 inches. In some embodiments, the bruising and/or skin discoloration can be reduced compared to a level of bruising and/or skin discoloration associated with subcutaneously administering to the treatment area of the subject a composition comprising about 0.23 mg/ml of the collagenase, wherein a total dose of about 0.84 mg of the collagenase is administered per treatment session using a three-injection technique at a depth of about 0.5 inches. In some embodiments, the bruising and/or skin discoloration is reduced compared to a level of bruising and/or skin discoloration associated with subcutaneously administering to the treatment area of the subject a composition comprising the collagenase, mannitol, sucrose, and tromethamine, wherein a total dose of about 0.84 mg of the collagenase is administered per treatment session using a three-injection technique at a depth of about 0.5 inches.

The methods of reducing bruising and/or skin discoloration associated with collagenase-mediated treatment of cellulite in a subject can comprise subcutaneously administering to a treatment area of the subject a total dose of about 0.21 mg of collagenase per treatment session, the collagenase having a concentration of about 0.12 mg/ml, to thereby reduce the bruising and/or skin discoloration associated with the collagenase-mediated treatment of cellulite in the subject. In some embodiments, the collagenase can be administered using a three-injection technique. In some embodiments, the collagenase can be administered at a depth of about 0.5 inches. Thus, the methods of reducing bruising and/or skin discoloration associated with collagenase-mediated treatment of cellulite in a subject can comprise subcutaneously administering to a treatment area of the subject a total dose of about 0.21 mg of collagenase per treatment session, the collagenase having a concentration of about 0.12 mg/ml, using a three-injection technique at a depth of about 0.5 inches to thereby reduce the bruising and/or skin discoloration associated with the collagenase-mediated treatment of cellulite in the subject. In some embodiments, the subject can receive more than one treatment session, wherein the treatment sessions are about 42 days apart. The bruising and/or skin discoloration can be reduced compared to a level of bruising and/or skin discoloration associated with administering QWO® according to its U.S. prescribing information. In some embodiments, the bruising and/or skin discoloration can be reduced compared to a level of bruising and/or skin discoloration associated with subcutaneously administering to the treatment area of the subject a total dose of about 0.42 mg of collagenase per treatment session using the three-injection technique at a depth of about 0.5 inches.

In some embodiments, the bruising and/or skin discoloration can be reduced compared to a level of bruising and/or skin discoloration associated with subcutaneously administering to the treatment area of the subject a total dose of about 0.42 mg of collagenase per treatment session, the collagenase having a concentration of about 0.23 mg/ml, using the three-injection technique at a depth of about 0.5 inches, wherein the subject received more than one treatment sessions that are about 42 days apart.

The methods of reducing bruising and/or skin discoloration associated with collagenase-mediated treatment of cellulite in a subject can comprise orally administering to the subject tranexamic acid and subcutaneously administering to a treatment area of the subject a total dose of about 0.84 mg of collagenase per treatment session to thereby reduce the bruising and/or skin discoloration associated with the collagenase-mediated treatment of cellulite in the subject. In some embodiments, the tranexamic acid has a concentration of about 500 mg to about 1500 mg. In some embodiments, the tranexamic acid has a concentration of about 1300 mg. Thus, the methods of reducing bruising and/or skin discoloration associated with collagenase-mediated treatment of cellulite in a subject can comprise orally administering to the subject about 1300 mg of tranexamic acid and subcutaneously administering to a treatment area of the subject a total dose of about 0.84 mg of collagenase per treatment session to thereby reduce the bruising and/or skin discoloration associated with the collagenase-mediated treatment of cellulite in the subject. In some embodiments, the collagenase can be administered using a three-injection technique. In some embodiments, the collagenase can be administered at a depth of about 0.5 inches. The methods of reducing bruising and/or skin discoloration associated with collagenase-mediated treatment of cellulite in a subject can comprise orally administering to the subject about 1300 mg of tranexamic acid and subcutaneously administering to a treatment area of the subject a total dose of about 0.84 mg of collagenase per treatment session using a three-injection technique at a depth of about 0.5 inches to thereby reduce the bruising and/or skin discoloration associated with the collagenase-mediated treatment of cellulite in the subject. In some embodiments, the collagenase can have a concentration of about 0.23 mg/ml. In some embodiments, the subject can receive more than one treatment session, wherein the treatment sessions are about 3 weeks apart. In some embodiments, the tranexamic acid is orally administered three times a day for five days during the first treatment session. In some aspects, during the first treatment session, the tranexamic acid is orally administered to the subject three times on the day before the administering of the collagenase, three times on the day of the administering of the collagenase, and on each of days 2, 3, and 4 after the administering of the collagenase. In some embodiments, the tranexamic acid is orally administered three times a day for five days during the second treatment session. In some aspects, during the second treatment session, the tranexamic acid is orally administered to the subject three times on the day before the administering of the collagenase, three times on the day of the administering of the collagenase, and on each of days 2, 3, and 4 after the administering of the collagenase. The bruising and/or skin discoloration can be reduced compared to a level of bruising and/or skin discoloration associated with administering QWO® according to its U.S. prescribing information. In some embodiments, the bruising and/or skin discoloration is reduced compared to a level of bruising and/or skin discoloration associated with subcutaneously administering to the treatment area of the subject a total dose of about 0.84 mg of collagenase per treatment session using the three-injection technique at a depth of 0.5 inches.

A reduction in the level of bruising and/or skin discoloration can include an at least one-point improvement (i.e., lowering) on the IABSS. Suitable reductions, include, for example, a severity rating of 4 to 3, a severity rating of 3 to 2, a severity rating of 2 to 1, a severity rating of 1 to 0, a severity rating of 4 to 2, a severity rating of 4 to 1, a severity rating of 4 to 0, and so on.

Methods of Treating Cellulite

Disclosed herein are methods of treating cellulite in a subject. The methods of treating cellulite in a subject can comprise subcutaneously administering to a treatment area of the subject a total dose of about 0.42 mg of collagenase per treatment session to thereby treat the cellulite in the subject. In some embodiments, the collagenase can be administered using a three-injection technique. In some embodiments, the collagenase can be administered at a depth of about 0.5 inches. Thus, the methods of treating cellulite in a subject can comprise subcutaneously administering to a treatment area of the subject a total dose of about 0.42 mg of collagenase per treatment session using a three-injection technique at a depth of about 0.5 inches to thereby treat the cellulite in the subject. In some embodiments, the collagenase has a concentration of about 0.23 mg/ml. In some embodiments, the collagenase can be a component of a composition/pharmaceutical formulation comprising the collagenase, mannitol, sucrose, and tromethamine. The composition/pharmaceutical formulation can further comprise HCl to adjust the pH as needed. The composition/pharmaceutical formulation can have a pH of approximately 8.0. In some embodiments, the subject can receive more than one treatment session, wherein the treatment sessions are about 3 weeks apart. In some embodiments, the subject can receive more than one treatment session, wherein the treatment sessions are about 42 days apart.

The methods of treating cellulite in a subject can comprise subcutaneously administering to a treatment area of the subject a total dose of about 0.84 mg of collagenase per treatment session, the collagenase having a concentration of about 0.05 mg/ml, to thereby treat the cellulite in the subject. In some embodiments, the collagenase can be administered using a three-injection technique. In some embodiments, the collagenase can be administered at a depth of about 0.5 inches. Thus, the methods of treating cellulite in a subject can comprise subcutaneously administering to a treatment area of the subject a total dose of about 0.84 mg of collagenase per treatment session, the collagenase having a concentration of about 0.05 mg/ml, using a three-injection technique at a depth of about 0.5 inches to thereby treat the cellulite in the subject. In some embodiments, the collagenase can be a component of a composition/pharmaceutical formulation comprising the collagenase, mannitol, sucrose, and tromethamine. The composition/pharmaceutical formulation can further comprise HCl to adjust the pH as needed. The composition/pharmaceutical formulation can have a pH of approximately 8.0. In some embodiments, the subject can receive more than one treatment session, wherein the treatment sessions are about 3 weeks apart.

The methods of treating cellulite in a subject can comprise subcutaneously administering to a treatment area of the subject a total dose of about 0.84 mg of collagenase per treatment session, the collagenase having a concentration of about 0.23 mg/ml, at a depth of about 0.25 inches to thereby treat the cellulite in the subject. In some embodiments, the collagenase can be administered using a three-injection technique. Thus, the methods of treating cellulite in a subject can comprise subcutaneously administering to a treatment area of the subject a total dose of about 0.84 mg of collagenase per treatment session, the collagenase having a concentration of about 0.23 mg/ml, using a three-injection technique at a depth of about 0.25 inches to thereby treat the cellulite in the subject. In some embodiments, the collagenase can be a component of a composition/pharmaceutical formulation comprising the collagenase, mannitol, sucrose, and tromethamine. The composition/pharmaceutical formulation can further comprise HCl to adjust the pH as needed. The composition/pharmaceutical formulation can have a pH of approximately 8.0. In some embodiments, the subject can receive more than one treatment session, wherein the treatment sessions are about 3 weeks apart.

The methods of treating cellulite in a subject can comprise subcutaneously administering to a treatment area of the subject a total dose of about 0.84 mg of collagenase per treatment session, the collagenase having a concentration of about 0.09 mg/ml, to thereby treat the cellulite in the subject. In some embodiments, the collagenase can be administered using a single aliquot injection. In some embodiments, the collagenase can be administered at a depth of about 0.25 inches. Thus, the methods of treating cellulite in a subject can comprise subcutaneously administering to a treatment area of the subject a total dose of about 0.84 mg of collagenase per treatment session, the collagenase having a concentration of about 0.09 mg/ml, using a single aliquot injection at a depth of about 0.25 inches to thereby treat the cellulite in the subject. In some embodiments, the collagenase can be a component of a composition/pharmaceutical formulation comprising the collagenase, mannitol, sucrose, and tromethamine. The composition/pharmaceutical formulation can further comprise HCl to adjust the pH as needed. The composition/pharmaceutical formulation can have a pH of approximately 8.0. In some embodiments, the subject can receive more than one treatment session, wherein the treatment sessions are about 3 weeks apart.

The number of injections administered via the single aliquot injection in a single treatment session is based, in part, on the severity of the cellulite and the size of the treatment area. One, two, three, four, five, six, seven, eight, nine, ten, 11, 12, 13, 14, 15, 16, 17, 18, 19.20, 25, 30, 35, 40, 45, 50, 55, 60, 65, 70, 75, 80, 85, 90, 95, 100, or greater than 100 injections can be administered to the treatment area in a single treatment session. In some embodiments, the administering comprises up to 30 single aliquot injections of the collagenase to the treatment area per treatment session.

When multiple injections are administered in a single treatment session, the injections can be evenly, or approximately evenly, spaced apart. The spacing between injections depends, in part, on the volume injected and the size of the treatment area. The injections, for example, can be about 0.25 cm, about 0.5 cm, about 0.75 cm, about 1.0 cm, about 1.25 cm, about 1.5 cm, about 1.75 cm, about 2.0 cm, about 2.25 cm, about 2.5 cm, about 2.75 cm, about 3.0 cm, about 3.25 cm, about 3.5 cm, about 3.75 cm, about 4.0 cm, or more than 4.0 cm apart. In some embodiments, the injections are spaced about 2 cm to about 3 cm apart.

When multiple injections are administered in a single treatment session, the injections can be administered at random sites within the treatment area, as one or more patterns within the treatment area, or at random sites and as one or more patterns within the treatment area. In some embodiments, the injections are spaced in a grid pattern as described herein.

Suitable volumes of each injection within the grid pattern include, for example, about 0.1 ml, about 0.2 ml, about 0.3 ml, about 0.4 ml, about 0.5 ml, about 0.6 ml, about 0.7 ml, about 0.8 ml, about 0.9 ml, or about 1.0 ml. In some embodiments, each injection has a volume of about 0.1 ml to 0.3 ml.

The methods of treating cellulite in a subject can comprise subcutaneously administering to a treatment area of the subject a composition comprising collagenase, lidocaine, and epinephrine, wherein a total dose of about 0.42 mg of the collagenase is administered per treatment session to thereby treat the cellulite in the subject. In some embodiments, the collagenase can be administered using a three-injection technique. In some embodiments, the collagenase can be administered at a depth of about 0.5 inches. Thus, the methods of treating cellulite in a subject can comprise subcutaneously administering to a treatment area of the subject a composition comprising collagenase, lidocaine, and epinephrine, wherein a total dose of about 0.42 mg of the collagenase is administered per treatment session using a three-injection technique at a depth of about 0.5 inches to thereby treat the cellulite in the subject. In some embodiments, the composition comprises 0.23 mg/ml collagenase, 2% lidocaine, and 1:200,000 epinephrine. In some embodiments, the subject can receive more than one treatment session, wherein the treatment sessions are about 3 weeks apart. In some embodiments, the composition further comprises mannitol, sucrose and tromethamine. Thus, the methods of treating cellulite in a subject can comprise subcutaneously administering to a treatment area of the subject a composition comprising collagenase, lidocaine, epinephrine, mannitol, sucrose, and tromethamine, wherein a total dose of about 0.42 mg of the collagenase is administered per treatment session using a three-injection technique at a depth of about 0.5 inches to thereby treat the cellulite in the subject.

The methods of treating cellulite in a subject can comprise subcutaneously administering to a treatment area of the subject a total dose of about 0.21 mg of collagenase per treatment session, the collagenase having a concentration of about 0.12 mg/ml, to thereby treat the cellulite in the subject. In some embodiments, the collagenase can be administered using a three-injection technique. In some embodiments, the collagenase can be administered at a depth of about 0.5 inches. Thus, the methods of treating cellulite in a subject can comprise subcutaneously administering to a treatment area of the subject a total dose of about 0.21 mg of collagenase per treatment session, the collagenase having a concentration of about 0.12 mg/ml, using a three-injection technique at a depth of about 0.5 inches to thereby treat the cellulite in the subject. In some embodiments, the subject can receive more than one treatment session, wherein the treatment sessions are about 42 days apart. In some embodiments, the collagenase can be a component of a composition/pharmaceutical formulation comprising the collagenase, mannitol, sucrose, and tromethamine. The composition/pharmaceutical formulation can further comprise HCl to adjust the pH as needed. The composition/pharmaceutical formulation can have a pH of approximately 8.0.

The methods of treating cellulite in a subject can comprise orally administering to the subject tranexamic acid and subcutaneously administering to a treatment area of the subject a total dose of about 0.84 mg of collagenase per treatment session to thereby treat the cellulite in the subject. In some embodiments, the tranexamic acid has a concentration of about 500 mg to about 1500 mg. In some embodiments, the tranexamic acid has a concentration of about 1300 mg. Thus, the methods of treating cellulite in a subject can comprise orally administering to the subject about 1300 mg of tranexamic acid and subcutaneously administering to a treatment area of the subject a total dose of about 0.84 mg of collagenase per treatment session to thereby treat the cellulite in the subject. In some embodiments, the collagenase can be administered using a three-injection technique. In some embodiments, the collagenase can be administered at a depth of about 0.5 inches. The methods of treating cellulite in a subject can comprise orally administering to the subject about 1300 mg of tranexamic acid and subcutaneously administering to a treatment area of the subject a total dose of about 0.84 mg of collagenase per treatment session using a three-injection technique at a depth of about 0.5 inches to thereby treat the cellulite in the subject. In some embodiments, the collagenase can have a concentration of about 0.23 mg/ml. In some embodiments, the subject can receive more than one treatment session, wherein the treatment sessions are about 3 weeks apart. In some embodiments, the tranexamic acid is orally administered three times a day for five days during the first treatment session. In some aspects, during the first treatment session, the tranexamic acid is orally administered to the subject three times on the day before the administering of the collagenase, three times on the day of the administering of the collagenase, and on each of days 2, 3, and 4 after the administering of the collagenase. In some embodiments, the tranexamic acid is orally administered three times a day for five days during the second treatment session. In some aspects, during the second treatment session, the tranexamic acid is orally administered to the subject three times on the day before the administering of the collagenase, three times on the day of the administering of the collagenase, and on each of days 2, 3, and 4 after the administering of the collagenase.

Treatment of cellulite can be established by a scale or measurement tool selected from the Hexsel Cellulite Severity Scale (Hexsel CSS). Hexsel Depression Depth Score, Likert Scale, Dimple Analysis, Clinician Reported Photonumeric Cellulite Severity Scale (CR-PCSS), Patient Reported Photonumeric Cellulite Severity Scale (PR-PCSS), Investigator Global Aesthetic Improvement Scale (I-GAIS), Subject Global Aesthetic Improvement Scale (S-GAIS). Patient Reported Cellulite Impact Scale (PR-CIS), PR-CIS Abbreviated, Subject Self-Rating Scale (SSRS). Subject Satisfaction with Cellulite Treatment (SSCT), Clinician assessment of cellulite severity (photography or other imagery), Body-Q, and a validated photonumeric or other scale used by clinicians and/or patients to assess cellulite severity, improvement, and/or patient satisfaction.

The Fitzpatrick Skin Scale is a 6-level scale (levels I-VI) for assessment of skin color and propensity for tanning to categorize skin types. The skin types range from level 1: Pale white skin, blue/hazel eyes, blond/red hair, always burns, does not tan, to level VI: Dark brown or black skin, never burns, always tans darkly. The investigator (or designee) will determine the Fitzpatrick Skin Type for all subjects at screening.

The Hexsel Cellulite Severity Scale (CSS) is a photonumeric scale used to assess 5 key morphologic features of cellulite: (A) number of evident depressions, (B) depth of depressions. (C) morphological appearance of skin surface alterations, (D) laxity, flaccidity or sagging of skin, and (E) current classification scale based on medical literature (Hexsel el al., 2009; Nürnberger and Müller, 1978). Each of these features is evaluated on a 4-point scale from a low of 0 to a high of 3 (as shown in Table 1).

TABLE 1

| Hexsel Cellulite Severity Scale | |
| --- | --- |
| A - Number of Evident Depressions | 0 = none/no depressions<br>1 = a small amount: 1-4 depressions are visible<br>2 = a moderate amount: 5-9 depressions<br>3 = a large amount: 10 or more depressions |
| B - Depth of Depressions | 0 = no depressions<br>1 = superficial depressions<br>2 = medium depth depressions<br>3 = deep depressions |
| C - Morphological Appearance of Skin Surface Alterations | 0 = no raised areas<br>1 = 'orange peel' appearance<br>2 = 'cottage cheese' appearance<br>3 = 'mattress' appearance |
| D - Grade of laxity, flaccidity, or sagging skin | 0 = absence of laxity, flaccidity, or sagging skin<br>1 = slight draped appearance<br>2 = moderate draped appearance<br>3 = severe draped appearance |
| E - Current classification scale based on the scale originally described by Nürnberger and Müller (1978) | 0 = Grade or Stage 0 = There is no alteration of the skin surface.<br>1 = Grade or Stage I = The skin of the affected area is smooth while the participant is standing or lying, but the alterations to the skin surface can be seen by pinching the skin or with muscle contraction.<br>2 = Grade or Stage II = The orange skin or mattress appearance is evident when standing, without the use of any manipulation (skin pinching or muscle contraction).<br>3 = Grade or Stage III = The alterations described in Grade or Stage II are present together with raised areas and nodules. |

The Clinician Reported Photonumeric Cellulite Severity Scale (CR-PCSS) is a validated 5-level photonumeric scale developed specifically for investigators and used by the investigator to assess the severity of the participant's cellulite in the treatment area (such as one or both buttocks) by live assessments. The ratings range from 0 (None) to 4 (Severe) with labels and descriptors to aid the investigator in the assessments. This assessment should be made while the participant is in the standing position with relaxed gluteus muscle %.

The Patient Reported Photonumeric Cellulite Severity Scale (PR-PCSS) is a validated 5-level photonumeric scale developed specifically for patients and used by the patients to assess the severity of their cellulite in the treatment area (such as one or both buttocks) by viewing digital images of each of their buttocks captured by photography. The ratings range from 0 (None) to 4 (Severe) with images, labels and descriptors to aid the patients in the assessments.

Investigator Global Aesthetic Improvement Scale (I-GAIS) is a 7-level scale ranging from 3 (very much improved) to −3 (very much worse)(Table 2). Investigators who are physicians will use the I-GAIS to determine the degree of improvement of each treatment area by comparing the cellulite from the Day 1 pretreatment (baseline) image of each treatment area to the images taken at the subsequent visits. The 1-GAIS assessments will be based on digital photographs and are performed separately for each of 2 treatment areas.

TABLE 2

| Investigator-Global Aesthetic Improvement Scale (I-GAIS) | | |
| --- | --- | --- |
| Rating | Response Option | Description |
| +3 | Very much improved | Optimal cosmetic result from treatment of the treated dimples |

TABLE 2-continued

Investigator-Global Aesthetic Improvement Scale (I-GAIS)

| Rating | Response Option | Description |
|---|---|---|
| +2 | Much improved | Marked improvement in the treated area appearance from before treatment, but not completely optimal |
| +1 | Improved | Obvious improvement in the treated area appearance from before treatment, but additional treatment is indicated |
| 0 | No change | The treated area appearance is essentially the same as before treatment |
| −1 | Worse | The treated area appearance is worse than before treatment |
| −2 | Much worse | Marked worsening in appearance from the initial condition |
| −3 | Very much worse | Obvious worsening in appearance from the initial condition |

Subject and Investigator Cellulite Assessments—Investigator cellulite assessments are independent of the subject assessments. Therefore, all subject cellulite assessments must be completed before the investigator's cellulite assessments are initiated. Subject assessments will occur while the subject is alone with no study site personnel in the room. Investigators will be instructed not to verbalize their ratings while in the presence of the subject and vice versa.

Subject Global Aesthetic Improvement Scale (S-GAIS) is a 7-level scale ranging from 3 (very much improved) to −3 (very much worse). Subjects will use the S-GAIS to determine the degree of improvement of each treatment area by comparing the cellulite from the Day 1 pretreatment (baseline) image of each treatment area to the images taken at the subsequent visits.

Body-Q Appraisal of Cellulite is a subset of questions from the Body-Q questionnaire that was developed to measure patient perceptions of weight loss and/or body contouring.

Investigator Satisfaction with Administration Scale (Likert scale) is a 5-point scale that can be used to determine investigator satisfaction with CCH (Investigator Satisfaction with CCH Administration).

Ultrasound Assessment—Surface ultrasound images of the treatment areas can be captured. Prespecified parameters can be measured/assessed from the images.

3-D Photography—The PRIMOS 3-D camera can be utilized as an exploratory tool to objectively quantify a skin surface roughness score. This equipment, and the associated imaging technology, presents a new way to capture changes in dermal laxity and resolution of skin dimpling due to cellulite.

Digital Photography can be taken with the subject standing in a consistent, standard relaxed pose, with relaxed gluteus muscles using the supplied Canfield camera system.

The treatment of cellulate can include an at least one-point improvement on any of the above scales. Using the CR-PCSS as an example, the treatment of cellulite includes a severity rating of 4 to 3, a severity rating of 3 to 2, a severity rating of 2 to 1, a severity rating of 1 to 0, a severity rating of 4 to 2, a severity rating of 4 to 1, a severity rating of 4 to 0, and so on.

In any of the herein disclosed methods the subject can receive multiple treatment sessions. The subject can receive, for example, one, two, three, four, five, six, seven, eight, nine, ten, or more than ten treatment sessions. In some embodiments, the treatment sessions are 3 weeks (21 days) apart. In some embodiments, the treatment sessions are 6 weeks (42 days) apart.

The amount of collagenase injected using the three-injection technique refers to the amount of collagenase in each of the three injected aliquots combined. The amount of collagenase injected using the single aliquot technique refers to the amount of collagenase in that single aliquot. The amount of collagenase administered per injection depends, in part, on the size of the treatment area, the severity of the cellulite, the injection technique (e.g., the three-injection technique or the single aliquot injection), and the volume administered per injection. Suitable amounts of collagenase administered to the treatment area per injection for any of the herein disclosed methods include, for example, about 0.0001 mg, about 0.001 mg, about 0.01 mg, about 0.02 mg, about 0.03 mg, about 0.035 mg, about 0.04 mg, about 0.05 mg, about 0.06 mg, about 0.07 mg, about 0.08 mg, about 0.09 mg, about 0.10 mg, about 0.20 mg, about 0.30 mg, about 0.40 mg, about 0.50 mg, about 0.60 mg, about 0.70 mg, about 0.80 mg, about 0.90 mg, about 1.0 mg, about 1.5 mg, about 2.0 mg, about 2.5 mg, about 3.0 mg, about 3.5 mg, about 4.0 mg, about 4.5 mg, about 5.0 mg, or more than 5.0 mg. The amount of collagenase administered per injection can be from about 0.0001 mg to about 5.0 mg, from about 0.001 mg to about 5.0 mg, from about 0.01 mg to about 5.0 mg, from about 0.05 mg to about 5.0 mg, from about 0.1 mg to about 5.0 mg, from about 0.5 mg to about 5.0 mg, from about 1.0 mg to about 5 mg, from about 2.5 mg to about 5.0 mg, from about 0.01 mg to about 2.5 mg, from about 0.01 mg to about 1.0 mg, from about 0.01 mg to about 0.5 mg, or from about 0.01 mg to about 0.1 mg. In some embodiments, about 0.028 mg of collagenase is administered per injection. In some embodiments, about 0.035 mg of collagenase is administered per injection. In some embodiments, about 0.07 mg of collagenase is administered per injection.

The amount of collagenase administered in a single treatment session depends, in part, on the size of the treatment area, the severity of the cellulite, the injection technique, the volume administered per injection, and the anticipated number of treatment sessions. Suitable amounts of collagenase administered to the treatment area in a single treatment session for any of the disclosed methods include, for example, about 0.01 mg, about 0.02 mg, about 0.03 mg, about 0.04 mg, about 0.05 mg, about 0.06 mg, about 0.07 mg, about 0.08 mg, about 0.09 mg, about 0.10 mg, about 0.20 mg, about 0.21 mg, about 0.30 mg, about 0.40 mg, about 0.42 mg, about 0.50 mg, about 0.60 mg, about 0.70 mg, about 0.80 mg, about 0.84 mg, about 0.90 mg, about 1.0 mg, about 2.0 mg, about 3.0 mg, about 4.0 mg, about 5.0 mg, about 6.0 mg, about 7.0 mg, about 8.0 mg, about 9.0 mg, about 10.0 mg, about 11.0 mg, about 12.0 mg, about 13.0 mg, about 14.0 mg, about 15.0 mg, about 16.0 mg, about 17.0 mg, about 18.0 mg, about 19.0 mg, about 20.0 mg, or greater than 20.0 mg. The amount of collagenase administered in a single treatment session can be from about 0.01 mg to about 20.0 mg, from about 0.01 mg to about 15.0 mg, from about 0.01 mg to about 10.0 mg, from about 0.01 mg to about 5.0 mg, from about 0.01 mg to about 1.0 mg, from about 0.01 mg to about 0.5 mg, from about 0.01 mg to about 0.05 mg, from about 0.05 mg to about 20 mg, from about 0.1 mg to about 20 mg, from about 0.5 mg to about 20 mg, from about 1.0 mg to about 20 mg, from about 2.5 mg to about 20 mg, from about 5.0 mg to about 20 mg, or from about 10 mg to about 20 mg. In some embodiments, about 0.21 mg to about 0.63 mg of collagenase is administered to the treatment area in a single treatment session. In some embodiments, about 0.27 mg to about 0.55 mg of collagenase is administered to the treatment area in a single treatment session. In some embodiments, about 0.21 mg of collagenase is administered to the treatment area in a single treatment session. In some embodiments, about 0.42 mg of collagenase is administered to the treatment area in a single treatment session. In some embodiments, about 0.84 mg of collagenase is administered to the treatment area in a single treatment session.

"Collagenase" refers to any of the following: (a) collagenase (including mutants) having activity as defined by EC 3.4.24.3 (www_brenda-enzymes.org/enzyne.php?ecno-3.4.24.3 (accessed Apr. 27, 2023); (b) collagenase produced by fermentation of *Clostridium histolyticum* (also known as *Hathewaya histolytica*); (c) CCH (as described herein); (d) collagenase having at least 50% sequence alignment with collagenase I (also referred as class I collagenase) as determined by BLAST: (e) collagenase having at least 50% sequence alignment with collagenase II (also referred as class II collagenase) as determined by BLAST; (f) collagenase produced by fermentation of other source organisms (i.e., non-*Clostridium histolyticum*), e.g., mammalian, crustacean, fungal, bacterial, or microbial collagenase; (g) collagenase obtained by recombinant techniques; (h) collagenase with a molecular mass from about 65 kDa to about 130 kDa; (i) collagenase designated as collagenase I (col I) or collagenase II (col I); (j) mixtures of collagenase I and II; (k) collagenase from strain JCM 1403 (ATCC 19401) or derivatives thereof; (1) collagenase from strain ATCC 21000 or derivatives thereof; (m) collagenase from ATCC 69334 or derivatives thereof; (n) collagenase from *C. perfringens*; (o) collagenase from *Vibrio alginolyticus*; (p) collagenase from *Streptomyces*; (q) collagenase from *Pseudomonas*; (r) collagenase from *Achromobacter iophagus*; (s) collagenase described by Worthington Biochemical Corp. (www_Worthington-biochem; "Product Highlights"); (t) collagenase described by Sigma-Aldrich (www_sigma-aldrich); (u) collagenase having one or more of the following characteristics:

$V_{max}$ (min$^{-1}$) of about 0.08 to 7.70 (SRC assay; as described in Int'l Pub. No. WO2020/058755), or about 0.3 to 30.5 (GPA assay; as described in Int'l Pub. No. WO2020/058755);

$K_M$ of about 4.1 to 410 nM (SRC assay), or about 0.03 to 3.1 mM (GPA assay).

$K_{cat}$ (sec$^{-1}$) of about 1.1 to 107 (SRC assay), or about 93 to 9.179 (GPA assay);

$1/K_{cat}$ (microseconds) of about 376 to 37,222 (SRC assay), or about 4 to 428 (GPA assay); or $K_{cat}/K_M$ (mM$^{-1}$ sec$^{-1}$) of about 5.140 to 508.814 (SRC assay), or about 60 to 5,934 (GPA assay);

(v) collagenase described by Nordmark Arzneimittel GmbH & Co. KG; (w) collagenase from strain 004; (x) biosimilars of collagenase component of QWO® or biosimilars of QWO® (y) biosimilars of collagenase component of XIAFLEX® or biosimilars of XIAFLEX®; or (z) equivalents or mixtures of any of the foregoing. Non-limiting examples of collagenases that may be used in the disclosure herein are described in U.S. Pat. Nos. 7,811,560, 9,757,435, 9,744,138, and Int'l Pub. No. WO2012/125948.

In some embodiments, the collagenase can comprise a collagenase I. A suitable collagenase I includes, for example, a collagenase I comprising an amino acid sequence having 90%, 91%, 92%, 93%, 94%, 95%, 96%, 97%, 98%, 99%, or 100% sequence identity to the amino acid sequence of SEQ ID NO: 1. In some aspects, the collagenase I comprises the amino acid sequence of SEQ ID NO: 1.

In some embodiments, the collagenase can comprise a collagenase II. A suitable collagenase II includes, for example, a collagenase II comprising an amino acid sequence having 90%, 91%, 92%, 93%, 94%, 95%, 96%, 97%, 98%, 99%, or 100% sequence identity to the amino acid sequence of SEQ ID NO: 2. In some aspects, the collagenase II comprises the amino acid sequence of SEQ ID NO: 2.

TABLE 3

| Sequences | |
| --- | --- |
| Collagenase I (SEQ ID NO: 1) | IANTNSEKYDFEYLNGLSYTELTNLIKNIKWNQINGLFNYSTGSOKFFG DKNRVQAIINALQESGRTYTANDMKGIETFTEVLRAGFYLGYYNDGLSY LNDRNFQDKCIPAMIAIQKNPNFKLGTAVQDEVITSLGKLIGNASANAE VVNNCVPVLKQFRENLNQYAPDYVKGTAVNELIKGIEFDFSGAAYEKDV KTMPWYGKIDPFINELKALGLYGNITSATEWASDVGIYYLSKEGLYSTN RNDIVQSLEKAVDMYKYGKIAFVAMERITWDYDGIGSNGKKVDHDKELD DAEKHYLPKTYTFDNGTFIIRAGEKVSEEKIKRLYWASREVKSQFHRVV GNDKALEVGNADDVLTMKIFNSPEEYKENTNINGVSTDNGGLYIEPRGT FYTYERTPQQSIFSLEELFRHEYTHYLQARYLVDGLWGOGPFYEKNRLT WFDEGTAEFFAGSTRTSGVLPRKSILGYLAKDKVDHRYSLKKTLNSGYD DSDWMFYNYGFAVAHYLYEKDMPTFIKMNKAILNTDVKSYDEIIKKLSD DANKNTEYQNHIQELADKYQGAGIPLVSDDYLKDHGYKKASEVYSEISK AASLTNTSVTAEKSQYFNTFTLRGTYTGETSKGEFKDWDEMSKKLDGTL ESLAKNSWSGYKTLTAYFTNYRVTSDNKVQYDVVFHGVLTDNADISNNK APIAKVTGPSTGAVGRNIEFSGKDSKDEDGKIVSYDWDFGDGATSRGKN SVHAYKKTGTYNVTLKVTDDKGATATESFTIEIKNEDTTTPITKEMEPN DDIKEANGPIVEGVTVKGDLNGSDDADTFYFDVKEDGDVTIELPYSGSS NFTWLVYKEGDDQNHIASGIDKNNSKVGTFKATKGRHYVFIYKHDSASN ISYSLNIKGLGNEKLKEKENNDSSDKATVIPNFNTTMQGSLLGDDSRDY YSFEVKEEGEVNIELDKKDEFGVTWTLHPESNINDRITYGQVDGNKVSN KVKLRPGKYYLLVYKYSGSGNYELRVNK |
| Collagenase II (SEQ ID NO: 2) | AVDKNNATAAVQNESKRYTVSYLKTLNYYDLVDLLVKTEIENLPDLFQY SSDAKEFYGNKTRMSFIMDEIGRRAPQYTEIDHKGIPTLVEVVRAGFYL GFHNKELNEINKRSFKERVIPSILAIQKNPNFKLGTEVQDKIVSATGLL AGNETAPPEVVNNFTPIIQDCIKNMDRYALDDLKSKALFNVLAAPTYDI TEYLRATKEKPENTPWYGKIDGFINELKKLALYGKINDNNSWIIDNGIY HIAPLGKLHSNNKIGIETLTEVMKIYPYLSMOHLQSADQIERHYDSKDA EGNKIPLDKFKKEGKEKYCPKTYTFDDGKVIIKAGARVEEEKVKRLYWA SKEVNSQFFRVYGIDKPLEEGNPDDILTMVIYNSPEEYKLNSVLYGYDT NNGGMYIEPDGTFFTYERKAEESTYTLEELFRHEYTHYLQGRYAVPGQW |

TABLE 3-continued

Sequences

```
GRTKLYDNDRLTWYEEGGAELFAGSTRTSGILPRKSIVSNIHNTTRNNR
YKLSDTVHSKYGASFEFYNYACMFMDYMYNKDMGILNKLNDLAKNNDVD
GYDNYIRDLSSNHALNDKYQDHMQERIDNYENLTVPFVADDYLVRHAYK
NPNEIYSEISEVAKLKDAKSEVKKSQYESTFTLRGSYTGGASKGKLEDQ
KAMNKFIDDSLKKLDTYSWSGYKTLTAYFTNYKVDSSNRVTYDVVFHGY
LPNEGDSKNSLPYGKINGTYKGTEKEKIKFSSEGSFDPDGKIVSYEWDF
GDGNKSNEENPEHSYDKVGTYTVKLKVTDDKGESSVSTTTAEIKDLSEN
KLPVIYMHVPKSGALNQKVVFYGKGTYDPDGSIAGYQWDFGDGSDESSE
QNPSHVYTKKGEYTVTLRVMDSSGQMSEKTMKIKITDPVYPIGTEKEPN
NSKETASGPIVPGIPVSGTIENTSDQDYFYFDVITPGEVKIDINKLGYG
GATWVVYDENNNAVSYATDDGQNLSGKFKADKPGRYYIHLYMENGSYMP
YRINIEGSVGR
```

In some embodiments, the collagenase can comprise a mixture of collagenase I and collagenase II. The collagenase can comprise, for example, a mixture of a collagenase I comprising an amino acid sequence having 90%, 91%, 92%, 93%, 94%, 95%, 96%, 97%, 98%, 99%, or 100% sequence identity to the amino acid sequence of SEQ ID NO: 1 and a collagenase II comprising an amino acid sequence having 90%, 91%, 92%, 93%, 94%, 95%, 96%, 97%, 98%, 99%, or 100% sequence identity to the amino acid sequence of SEQ ID NO: 2. In some aspects, the collagenase comprises a mixture of the collagenase I comprising the amino acid sequence of SEQ ID NO: 1 and the collagenase II comprising the amino acid sequence of SEQ ID NO: 2. Suitable mixtures of the collagenase I and collagenase II include, for example, a collagenase I:collagenase II mass ratio of 0.1:1, 0.25:1, 0.5:1, 0.75:1, 1:1, 1.1:1, 1.25:1, 1.5:1, 1.75:1, 2:1, 1:0.1, 1:0.25, 1:0.5; 1:0.75, 1:1.1, 1:1.25, 1:1.5, 1:1.75, or 1:2. Each of the collagenase I and collagenase II may have a purity of at least 80%, 85%, 90%, 91%, 92%, 93%, 94%, 95%, 96%, 97%, 98%, 99%, or 100% as measured by, for example, reverse phase HPLC.

In some embodiments, the collagenase can comprise collagenase *Clostridium histolyticum* (CCH). "CCH," as used herein, refers to collagenase *Clostridium histolyticum* containing a mixture of collagenase I (SEQ ID NO: 1) and collagenase II (SEQ ID NO: 2) in an approximate 1:1 mass ratio. CCH is obtained by the fermentation of *Clostridium histolyticum* (also known as *Hathewaya histolytica*).

In some embodiments, the collagenase I and collagenase II can have the following characteristics:

Collagenase I (SRC Microplate Assay)
$V_{max}$: About 0.08 to 7.70 min$^{-1}$
$K_M$: About 4.1 to 410 nanoMolar
$K_{cat}$: About 1.1 to 107 sec$^{-1}$
$1/K_{cat}$: About 376 to 37,222 microseconds
$K_{cat}/K_M$: About 5,140 to 508,814 mM$^{-1}$ sec$^{-1}$ Collagenase II (GPA Microplate Assay)
$V_{max}$: About 0.3 to 30.5 min$^{-1}$
$K_M$: About 0.03 to 3.1 mM
$K_{cat}$: About 93 to 9,179 sec$^{-1}$
$1/K_{cat}$: About 4 to 428 microseconds
$K_{cat}/K_M$: About 60 to 5.934 mM$^{-1}$ sec$^{-1}$ In some embodiments, the collagenase I and collagenase II can have the following characteristics:

Collagenase I (SRC Assay):
$V_{max}$: About 3.8 min$^{-1}$
$K_M$: About 2.07×10$^{-4}$ mM
$K_{cat}$: About 53 sec$^{-1}$
$1/K_{cat}$: About 18.799 microseconds
$k_{cat}/K_M$: About 256.977 mM$^{-1}$ sec$^{-1}$ Collagenase II (GPA Assay):
$V_{max}$: About 15.4 min$^{-1}$
$K_M$: About 1.6 mM
$K_{cat}$: About 4,636 sec$^{-1}$
$1/K_{cat}$: About 216 microseconds
$k_{cat}/K_M$: About 2,997 mM$^{-1}$ sec$^{-1}$ Collagenase-Containing Formulations Disclosed herein are formulations comprising: a collagenase; lidocaine; and epinephrine.

Any of the above described collagenases can be used in the formulations. In some embodiments, the collagenase can comprise a collagenase I. In some embodiments, the collagenase can comprise a collagenase II. In some embodiments, the collagenase can comprise a mixture of collagenase I and collagenase II. In some aspects, the collagenase comprises a mixture of the collagenase I comprising the amino acid sequence of SEQ ID NO: 1 and the collagenase II comprising the amino acid sequence of SEQ ID NO: 2. In some embodiments, the collagenase can comprise collagenase *Clostridium histolyticum* (CCH).

The collagenase can have a concentration of about 0.23 mg/ml. The lidocaine can have a concentration of about 5 mg/mL, about 10 mg/mL, about 15 mg/mL, or about 20 mg/mL. The epinephrine can have a concentration of about 5 mcg/mL or about 10 mcg/mL. In some embodiments, the formulation can comprise about 0.23 mg/ml of collagenase, about 2% of lidocaine, and about 1:200,000 epinephrine.

The formulation can further comprise mannitol, sucrose, and tromethamine. Thus, in some embodiments, the formulation comprises a collagenase, lidocaine, epinephrine mannitol, sucrose, and tromethamine.

EXAMPLES

The following examples are provided to further describe some of the embodiments disclosed herein. The examples are intended to illustrate, not to limit, the disclosed embodiments.

Example 1—Aphrodite-1 Study

Background

Collagenase *Clostridium histolyticum*-aaes (CCH-aaes; QWO®. Endo Aesthetics LLC) for injection is indicated for the treatment of moderate to severe cellulite in the buttocks of adult women. CCH-aaes injection is believed to initiate Enzymatic Subcision and Remodeling® including lysis of the mature, collagen-rich septae that cause the characteristic dimpling of cellulite, rapid onset of neocollagenesis, and some degree of fat lobule reorganization (to smaller, more uniformly sized lobules). Injection-site bruising was the most common adverse event reported in a pooled analysis of two identically designed randomized, phase 3 trials in women with cellulite in the buttocks treated with CCH-aaes (84%) or placebo (21%). During these trials, 0.84 mg of CCH-aaes was administered per treatment area using a ½-inch, three-aliquot technique (also referred to as the three-injection technique as illustrated in FIG. 1). Although injection-site bruising following CCH-aaes administration generally resolved within 14 to 21 days, bruising was bothersome to some women and may be related to subsequent skin discoloration. Therefore, a trial was designed to identify potential interventions that may mitigate bruising and its associated consequences.

Objective

To assess, using a self-control study design, the effects of several interventions on prevention or reduction of bruising of the buttocks of women with moderate to severe cellulite after treatment with CCH-aaes injection.
Methods Study Design and Interventions APHRODITE-1 (a phase 2, open-label, self-controlled study of different interventions to reduce bruising following CCH-eaes treatment) aimed to enroll up to 150 women during this first phase of the trial. The trial was designed to assess different CCH-aaes doses, different CCH-aaes concentrations, different injection techniques (including injection depth), and diluent additives in an effort to prevent or decrease injection-site bruising. The study was designed to enable the addition of new intervention cohorts, if desired in a later phase of the study, with the consideration of other diluent additives, alternate doses, and injection timing variables, including:

Different CCH-aaes doses or different concentrations;
Different injection techniques (including injection depth);
Inclusion of diluent additives; and/or
Addition of new intervention cohorts.

Up to 30 participants were allocated (1:1:1:1:1:1 ratio) to each of 8 cohorts using an interactive response technology system as shown in Table 4:

TABLE 4

| | | Study Intervention Cohorts | |
| --- | --- | --- | --- |
| | Women, | | Intervention* |
| Cohort | (n) | Left buttock—investigational side | Right buttock—control side |
| 1 | 15-30 | Labeled injection technique (3 aliquots) | Labeled injection technique (3 aliquots) |
| | | Half (50%) of labeled CCH-aaes dose (0.42 mg) | Labeled CCH-aaes dose (0.84 mg) |
| | | Labeled CCH-aaes concentration (0.23 mg/mL) | Labeled CCH-aaes concentration (0.23 mg/mL) |
| 2 | 15-30 | Labeled injection technique (3 aliquots) | Labeled injection technique (3 aliquots) |
| | | Labeled CCH-aaes dose (0.84 mg) | Labeled CCH-aaes dose (0.84 mg) |
| | | ~5-fold dilution of labeled CCH-aaes concentration (0.05 mg/mL) | Labeled CCH-aaes concentration (0.23 mg/mL) |
| 3 | 15-30 | Labeled injection technique (3 aliquots) | Labeled injection technique (3 aliquots) |
| | | ¼-inch injection depth | Labeled ½-inch injection depth |
| | | Labeled CCH-aaes dose (0.84 mg) | Labeled CCH-aaes dose (0.84 mg) |
| | | Labeled CCH-aaes concentration (0.23 mg/mL) | Labeled CCH-aaes concentration (0.23 mg/mL) |
| 4 | 15-30 | Single aliquot at ¼-inch depth per injection (up to 30 injections) | Single aliquot at ¼-inch depth per injection (up to 12 injections) |
| | | Labeled CCH-aaes dose (0.84 mg) | Labeled CCH-aaes dose (0.84 mg) |
| | | ~2.5-fold dilution of labeled CCH-aaes concentration (0.09 mg/mL) | Labeled CCH-aaes concentration (0.23 mg/mL) |
| 5 | 15-30 | Labeled injection technique (3 aliquots) | Labeled injection technique (3 aliquots) |
| | | Half of labeled CCH-aaes dose (0.42 mg) | Labeled CCH-aaes dose (0.84 mg) |
| | | Lidocaine 2% and epinephrine 1:200,000 as diluent additive | Product-supplied standard diluent (a sterile, preservative-free, colorless solution of 0.03% calcium chloride dihydrate in 0.6% sodium chloride, and Water for Injection) |
| | | Labeled CCH-aaes concentration (0.23 mg/mL) | Labeled CCH-aaes concentration (0.23 mg/mL) |
| 6 | 15-30 | Labeled injection technique (3 aliquots) | Labeled injection technique (3 aliquots) |
| | | One-quarter of labeled dose (0.21 mg) | Half of labeled dose (0.42 mg) |
| | | Half of labeled concentration (0.12 mg/ml) | Labeled concentration (0.23 mg/ml) |
| | | 2 treatments administered approximately 42 days apart | 2 treatments administered approximately 42 days apart |

TABLE 4-continued

| | | Study Intervention Cohorts | |
| | | | |
| | Women, | | Intervention* |
| Cohort | (n) | Left buttock—investigational side | Right buttock—control side |
| 7a | 15 | Labeled injection technique (3 aliquots) Labeled CCH-aaes dose (0.84 mg/side) Labeled CCH-aaes concentration (0.23 mg/mL) 1300 mg oral tranexamic acid three times a day (TID) for 5 days (on Day −1, prior to the day of the first injection on Day 1 and for the 3 days after the first injection of CCH-aaes (on Days 2-4), during the first treatment session. | Labeled injection technique (3 aliquots) Labeled CCH-aaes dose (0.84 mg/side) Labeled CCH-aaes concentration (0.23 mg/mL) of QWO (CCH-aaes) |
| 7b | 15 | Investigational side will not receive CCH-aaes during the first treatment session Labeled injection technique (3 aliquots) during second treatment session Labeled CCH-aaes dose (0.84 mg/side) during second treatment session Labeled CCH-aaes concentration (0.23 mg/mL) during second treatment session 1300 mg oral tranexamic acid TID for 5 days (prior to the day of the first injection on Day 21, the day of the first injection, Day 22. and for the 3 days following the first injection on Days 23-25) during the second treatment session. | Labeled injection technique (3 aliquots) Labeled CCH-aaes dose (0.84 mg/side) Labeled CCH-aaes concentration (0.23 mg/mL) |

*CCH-aaes dose is per buttock; "labeled" means per QWO ® US Prescribing Information. CCH-aaes = collagenase *Clostridium histolyticum*
"Labeled injection technique" refers to the "three-injection technique" as described herein
All participants in Cohort 7 received a maximum dose of up to 0.84 mg of CCH-aaes on the control side and a maximum dose of up to 0.84 mg of CCH-aaes to the investigational side per treatment session ×3 treatment sessions for a maximum total dose of 5.04 mg.
Participants in Cohort 7a had the investigational side treated on Days 1, 22, and 43 with the control side treated on Days 22, 43 and 64. Treatment was staggered for participants in Cohort 7b vs Cohort 7a: the investigational side treated on Days 22, 43, and 64 and the control side treated on Days 1, 22, and 43. Tranexamic acid was provided by the sponsor and self-administered by all participants enrolled in Cohort 7. Participants in Cohort 7a took tranexamic acid 1300 mg orally TID for 5 days (prior to the day of the first injection of CCH-aaes of the investigational buttock (Day −1), the day of the first injection (Day 1) and for the 3 days following the first injection (Days 2 to 4). Participants in Cohort 7b took tranexamic acid orally TID for 5 days (prior to the day of the second injection on Day 21, the day of the second injection (Day 22) and for the 3 days following the second injection (Day 23 to Day 25). All participants in Cohort 7, had an additional treatment visit on Day 64.

45

The patient population included:
Up to 180 women aged 18-60 years old.
Body mass index (BMI) of 18 to <32 kg/m²;
Moderate to severe cellulite on both buttocks (CR-PCSS rating of 3 or 4);

Hexsel CSS total score of ≤12; and
Fitzpatrick skin type of category I-IV.
Table 5 provides a summary of the demographic and baseline characteristics for those subjects that were enrolled in the study.

TABLE 5

| | | | | | Demographic and Baseline Characteristics | | | | | |
| | Statistic | Cohort 1 (N = 22) | Cohort 2 (N = 14) | Cohort 3 (N = 5) | Cohort 4 (N = 7) | Cohort 5 (N = 10) | Cohort 6 (N = 19) | Cohort 7a (N = 7) | Cohort 7b (N = 7) | Overall (N = 91) |
| Age (Years) | n | 22 | 14 | 5 | 7 | 10 | 19 | 7 | 7 | 91 |
| | Mean | 43.50 | 44.79 | 44.40 | 34.00 | 46.50 | 47.74 | 37.57 | 38.57 | 43.40 |
| | SD | 10.698 | 9.125 | 8.503 | 8.699 | 10.179 | 7.225 | 10.967 | 10.549 | 19.998 |
| | Median | 44.00 | 44.50 | 40.00 | 37.00 | 45.00 | 50.00 | 35.00 | 41.00 | 43.00 |
| | Min | 22.0 | 29.0 | 36.0 | 25.0 | 32.0 | 31.0 | 26.0 | 25.0 | 22.0 |
| | Max | 60.0 | 57.0 | 55.0 | 47.0 | 60.0 | 57.0 | 58.0 | 52.0 | 60.0 |
| Age Group | | | | | | | | | | |
| 18-<30 Years | n (%) | 2 (9.1) | 2 (14.3) | 0 (0.0) | 3 (42.9) | 0 (0.0) | 0 (0.0) | 2 (28.6) | 2 (28.6) | 11 (12.1) |
| 30-<45 Years | n (%) | 9 (40.9) | 5 (35.7) | 3 (60.0) | 3 (42.9) | 5 (50.0) | 6 (31.6) | 4 (57.1) | 3 (42.9) | 38 (41.8) |
| 45-60 Years | n (%) | 11 (50.0) | 7 (50.0) | 2 (40.0) | 1 (14.3) | 5 (50.0) | 13 (68.4) | 1 (14.3) | 2 (28.6) | 42 (46.2) |

TABLE 5-continued

| | | Demographic and Baseline Characteristics | | | | | | | | |
|---|---|---|---|---|---|---|---|---|---|---|
| | Statistic | Cohort 1 (N = 22) | Cohort 2 (N = 14) | Cohort 3 (N = 5) | Cohort 4 (N = 7) | Cohort 5 (N = 10) | Cohort 6 (N = 19) | Cohort 7a (N = 7) | Cohort 7b (N = 7) | Overall (N = 91) |
| Gender | | | | | | | | | | |
| Female | n (%) | 22 (100.0) | 14 (100.0) | 5 (100.0) | 7 (100.0) | 10 (100.0) | 19 (100.0) | 7 (100.0) | 7 (100.0) | 91 (100.0) |
| Race | | | | | | | | | | |
| American Indian or Alaska Native | n (%) | 0 (0.0) | 0 (0.0) | 0 (0.0) | 0 (0.0) | 0 (0.0) | 0 (0.0) | 0 (0.0) | 0 (0.0) | 0 (0.0) |
| Asian | n (%) | 0 (0.0) | 0 (0.0) | 0 (0.0) | 0 (0.0) | 0 (0.0) | 0 (0.0) | 1 (14.3) | 0 (0.0) | 1 (1.1) |
| Black or African American | n (%) | 1 (4.5) | 0 (0.0) | 0 (0.0) | 0 (0.0) | 0 (0.0) | 0 (0.0) | 0 (0.0) | 0 (0.0) | 1 (1.1) |
| Native Hawaiian or Other Pacific Islander | n (%) | 0 (0.0) | 0 (0.0) | 0 (0.0) | 0 (0.0) | 0 (0.0) | 0 (0.0) | 0 (0.0) | 0 (0.0) | 0 (0.0) |
| White | n (%) | 18 (81.8) | 14 (100.0) | 5 (100.0) | 7 (100.0) | 9 (90.0) | 18 (94.7) | 6 (85.7) | 7 (100.0) | 84 (92.3) |
| Other | n (%) | 1 (4.5) | 0 (0.0) | 0 (0.0) | 0 (0.0) | 0 (0.0) | 0 (0.0) | 0 (0.0) | 0 (0.0) | 1 (1.1) |
| Not Reported | n (%) | 0 (0.0) | 0 (0.0) | 0 (0.0) | 0 (0.0) | 0 (0.0) | 0 (0.0) | 0 (0.0) | 0 (0.0) | 0 (0.0) |
| Multiple | n (%) | 2 (9.1) | 0 (0.0) | 0 (0.0) | 0 (0.0) | 1 (10.0) | 1 (5.3) | 0 (0.0) | 0 (0.0) | 4 (4.4) |
| Unknown | n (%) | 0 (0.0) | 0 (0.0) | 0 (0.0) | 0 (0.0) | 0 (0.0) | 0 (0.0) | 0 (0.0) | 0 (0.0) | 0 (0.0) |
| Ethnicity | | | | | | | | | | |
| Hispanic or Latino | n (%) | 9 (40.9) | 5 (35.7) | 0 (0.0) | 1 (14.3) | 1 (10.0) | 4 (21.1) | 0 (0.0) | 0 (0.0) | 20 (22.0) |
| Not Hispanic and Non-Latino | n (%) | 7 (31.8) | 9 (64.3) | 5 (100.0) | 6 (85.7) | 5 (50.0) | 14 (73.7) | 7 (100.0) | 7 (100.0) | 60 (65.9) |
| Not Reported | n (%) | 6 (27.3) | 0 (0.0) | 0 (0.0) | 0 (0.0) | 4 (40.0) | 1 (5.3) | 0 (0.0) | 0 (0.0) | 11 (12.1) |
| Weight (kg) | n | 22 | 14 | 5 | 7 | 10 | 19 | 7 | 7 | 91 |
| | Mean | 69.267 | 71.021 | 69.028 | 69.194 | 70.794 | 70.491 | 62.874 | 62.597 | 68.936 |
| | SD | 10.5376 | 8.6714 | 8.9555 | 9.6035 | 10.8925 | 9.1008 | 6.4246 | 6.1304 | 9.3678 |
| | Median | 68.855 | 71.145 | 72.580 | 70.400 | 70.130 | 70.220 | 63.320 | 63.500 | 68.770 |
| | Min | 51.30 | 58.51 | 56.79 | 56.06 | 58.97 | 50.98 | 55.16 | 54.98 | 50.98 |
| | Max | 88.00 | 82.10 | 77.47 | 85.19 | 89.45 | 85.28 | 73.39 | 72.12 | 89.45 |
| Height (cm) | n | 22 | 14 | 5 | 7 | 10 | 19 | 7 | 7 | 91 |
| | Mean | 161.764 | 168.184 | 166.014 | 168.003 | 167.640 | 164.659 | 165.100 | 165.246 | 165.240 |
| | SD | 8.8247 | 7.7285 | 7.8076 | 7.5389 | 6.6667 | 7.7048 | 3.5921 | 9.6011 | 7.8906 |
| | Median | 162.560 | 166.370 | 167.640 | 170.180 | 166.370 | 165.100 | 165.100 | 160.020 | 165.100 |
| | Min | 132.08 | 152.40 | 154.94 | 154.94 | 154.94 | 152.40 | 160.02 | 154.94 | 132.08 |
| | Max | 173.23 | 177.80 | 175.26 | 175.26 | 177.80 | 178.56 | 170.18 | 177.80 | 178.56 |
| BMI (kg/m$^2$) | n | 22 | 14 | 5 | 7 | 10 | 19 | 7 | 7 | 91 |
| | Mean | 26.50 | 25.22 | 25.00 | 24.64 | 25.21 | 26.12 | 23.14 | 22.99 | 25.33 |
| | SD | 3.319 | 3.275 | 1.323 | 3.635 | 3.458 | 3.684 | 2.417 | 1.233 | 3.285 |
| | Median | 26.10 | 25.40 | 25.10 | 23.90 | 24.25 | 25.90 | 22.20 | 22.90 | 24.90 |
| | Min | 21.1 | 19.1 | 23.7 | 19.4 | 21.2 | 20.9 | 20.5 | 21.5 | 19.1 |
| | Max | 31.6 | 30.9 | 27.0 | 29.8 | 31.0 | 32.0 | 27.8 | 24.8 | 32.0 |
| Skin Category (Fitzpatrick Scale) | | | | | | | | | | |
| I (Pale White) | n (%) | 1 (4.5) | 0 (0.0) | 0 (0.0) | 0 (0.0) | 1 (10.0) | 0 (0.0) | 0 (0.0) | 1 (14.3) | 3 (3.3) |
| II (Fair) | n (%) | 7 (31.8) | 8 (57.1) | 2 (40.0) | 4 (57.1) | 4 (40.0) | 11 (57.9) | 2 (28.6) | 6 (85.7) | 44 (48.4) |
| III (Darker White) | n (%) | 7 (31.8) | 3 (21.4) | 3 (60.0) | 2 (28.6) | 5 (50.0) | 6 (31.6) | 4 (57.1) | 0 (0.0) | 30 (33.0) |
| IV (Light Brown) | n (%) | 7 (31.8) | 3 (21.4) | 0 (0.0) | 1 (14.3) | 0 (0.0) | 2 (10.5) | 1 (14.3) | 0 (0.0) | 14 (15.4) |
| V (Brown) | n (%) | 0 (0.0) | 0 (0.0) | 0 (0.0) | 0 (0.0) | 0 (0.0) | 0 (0.0) | 0 (0.0) | 0 (0.0) | 0 (0.0) |
| VI (Dark Brown or (Black) | n (%) | 0 (0.0) | 0 (0.0) | 0 (0.0) | 0 (0.0) | 0 (0.0) | 0 (0.0) | 0 (0.0) | 0 (0.0) | 0 (0.0) |
| Time Since Last Menstrual Period (days) [1] | n | 22 | 14 | 5 | 7 | 10 | 19 | 6 | 7 | 190 |
| | Mean | 839.68 | 816.71 | 145.80 | 33.71 | 1279.90 | 945.21 | 272.17 | 380.29 | 732.50 |
| | SD | 1657.298 | 1525.703 | 273.816 | 6.676 | 1712.276 | 1511.931 | 569.675 | 790.396 | 1392.728 |
| | Median | 41.50 | 38.00 | 29.00 | 35.00 | 139.50 | 50.00 | 40.50 | 43.00 | 40.00 |
| | Min | 13.0 | 6.0 | 7.0 | 22.0 | 13.0 | 14.0 | 36.0 | 8.0 | 6.0 |
| | Max | 7199.0 | 5716.0 | 635.0 | 10.0 | 4453.0 | 5706.0 | 1435.0 | 2158.0 | 7199.0 |

TABLE 5-continued

| | | Demographic and Baseline Characteristics | | | | | | | | |
|---|---|---|---|---|---|---|---|---|---|---|
| | Statistic | Cohort 1 (N = 22) | Cohort 2 (N = 14) | Cohort 3 (N = 5) | Cohort 4 (N = 7) | Cohort 5 (N = 10) | Cohort 6 (N = 19) | Cohort 7a (N = 7) | Cohort 7b (N = 7) | Overall (N = 91) |
| Cellulite History [2] | | | | | | | | | | |
| Started ≥5 Years Ago | n (%) | 12 (54.5) | 9 (64.3) | 5 (100.0) | 2 (28.6) | 0 (0.0) | 15 (78.9) | 4 (57.1) | 3 (42.9) | 50 (54.9) |
| Started <5 Years Ago | n (%) | 5 (22.7) | 0 (0.0) | 0 (0.0) | 0 (0.0) | 3 (30.0) | 0 (0.0) | 2 (28.6) | 0 (0.0) | 10 (11.0) |
| Alcohol Use | | | | | | | | | | |
| Never | n (%) | 7 (31.8) | 9 (64.3) | 0 (0.0) | 0 (0.0) | 1 (10.0) | 2 (10.5) | 1 (14.3) | 3 (42.9) | 23 (25.3) |
| Current | n (%) | 13 (59.1) | 4 (28.6) | 5 (100.0) | 6 (85.7) | 8 (80.0) | 16 (84.2) | 6 (85.7) | 4 (57.1) | 62 (68.1) |
| Former | n (%) | 2 (9.1) | 1 (7.1) | 0 (0.0) | 1 (14.3) | 1 (10.0) | 1 (5.3) | 0 (0.0) | 0 (0.0) | 6 (6.6) |
| Tobacco Use | | | | | | | | | | |
| Never | n (%) | 16 (72.7) | 12 (85.7) | 5 (100.0) | 6 (85.7) | 6 (60.0) | 15 (78.9) | 4 (57.1) | 6 (85.7) | 70 (76.9) |
| Current | n (%) | 2 (9.1) | 0 (0.0) | 0 (0.0) | [0 (0.0) | 1 (10.0) | 0 (0.0) | 0 (0.0) | 1 (14.3) | 4 (4.4) |
| Former | n (%) | 4 (18.2) | 2 (14.3) | 0 (0.0) | 1 (14.3) | 3 (30.0) | 4 (21.1) | 3 (42.9) | 0 (0.0) | 17 (18.7) |
| IABSS Ratings at Visit 1 (Day 1) Left Buttock | | | | | | | | | | |
| 0 (None or almost no bruising) | n (%) | 22 (100.0) | 14 (100.0) | 5 (100.0) | 7 (100.0) | 10 (100.0) | 19 (100.0) | 7 (100.0) | 7 (100.0) | 91 (100.0) |
| 1 (Mild bruising) | n (%) | 0 (0.0) | 0 (0.0) | 0 (0.0) | 0 (0.0) | 0 (0.0) | 0 (0.0) | 0 (0.0) | 0 (0.0) | 0 (0.0) |
| 2 (Moderate bruising) | n (%) | 0 (0.0) | 0 (0.0) | 0 (0.0) | 0 (0.0) | 0 (0.0) | 0 (0.0) | 0 (0.0) | 0 (0.0) | 0 (0.0) |
| 3 (Severe bruising) | n (%) | 0 (0.0) | 0 (0.0) | 0 (0.0) | 0 (0.0) | 0 (0.0) | 0 (0.0) | 0 (0.0) | 0 (0.0) | 0 (0.0) |
| 4 (Very severe bruising) | n (%) | 0 (0.0) | 0 (0.0) | 0 (0.0) | 0 (0.0) | 0 (0.0) | 0 (0.0) | 0 (0.0) | 0 (0.0) | 0 (0.0) |
| | Mean | 0.00 | 0.00 | 0.00 | 0.00 | 0.00 | 0.00 | 0.00 | 0.00 | 0.00 |
| | SD | 0.000 | 0.000 | 0.000 | 0.000 | 0.000 | 0.000 | 0.000 | 0.000 | 0.000 |
| Right Buttock | | | | | | | | | | |
| 0 (None or almost no bruising) | n (%) | 22 (100.0) | 14 (100.0) | 5 (100.0) | 7 (100.0) | 10 (100.0) | 19 (100.0) | 7 (100.0) | 7 (100.0) | 91 (100.0) |
| 1 (Mild bruising) | n (%) | 0 (0.0) | 0 (0.0) | 0 (0.0) | 0 (0.0) | 0 (0.0) | 0 (0.0) | 0 (0.0) | 0 (0.0) | 0 (0.0) |
| 2 (Moderate bruising) | n (%) | 0 (0.0) | 0 (0.0) | 0 (0.0) | 0 (0.0) | 0 (0.0) | 0 (0.0) | 0 (0.0) | 0 (0.0) | 0 (0.0) |
| 3 (Severe bruising) | n (%) | 0 (0.0) | 0 (0.0) | 0 (0.0) | 0 (0.0) | 0 (0.0) | 0 (0.0) | 0 (0.0) | 0 (0.0) | 0 (0.0) |
| 4 (Very severe bruising) | n (%) | 0 (0.0) | 0 (0.0) | 0 (0.0) | 0 (0.0) | 0 (0.0) | 0 (0.0) | 0 (0.0) | 0 (0.0) | 0 (0.0) |
| | Mean | 0.00 | 0.00 | 0.00 | 0.00 | 0.00 | 0.00 | 0.00 | 0.00 | 0.00 |
| | SD | 0.000 | 0.000 | 0.000 | 0.000 | 0.000 | 0.000 | 0.000 | 0.000 | 0.000 |

[1] Time Since Last Menstrual Period (days) = Date of Day 1-Date of Last Menstrual Period.
[2] Years (≥5 or <5) = Day of Screening-Start Date of Cellulite History.
Note:
BMI = Body Mass Index.
IABSS = Investigator Assessment of Bruising Severity Scale.
SD = Standard Deviation.
Demographics and baseline characteristics are collected at Screening.
Percentages are based on the number of participants ('N') in each column.
Full Analysis Set (FAS) is defined as all participants in the Safety Population who have at least 1 valid IABSS assessment at a treatment area after an injection of QWO (CCH-aaes).

Figure 4A:
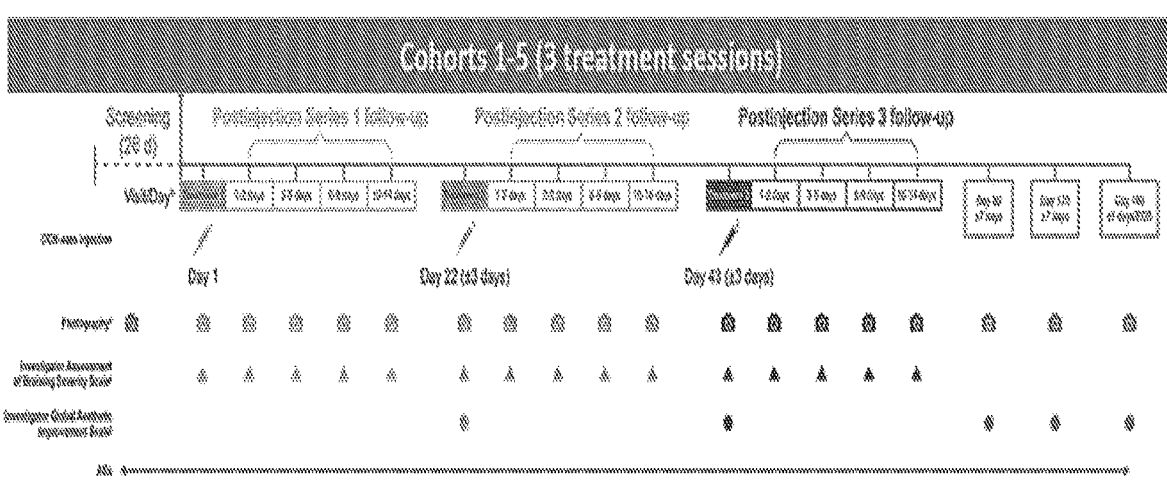
FIG. 4A and FIG. 4B illustrate exemplary schedules of assessments for the APHRODITE-I Study for Cohorts 1 to 5 (FIG. 4A) and Cohort 6 (FIG. 4B).
Figure 4B:
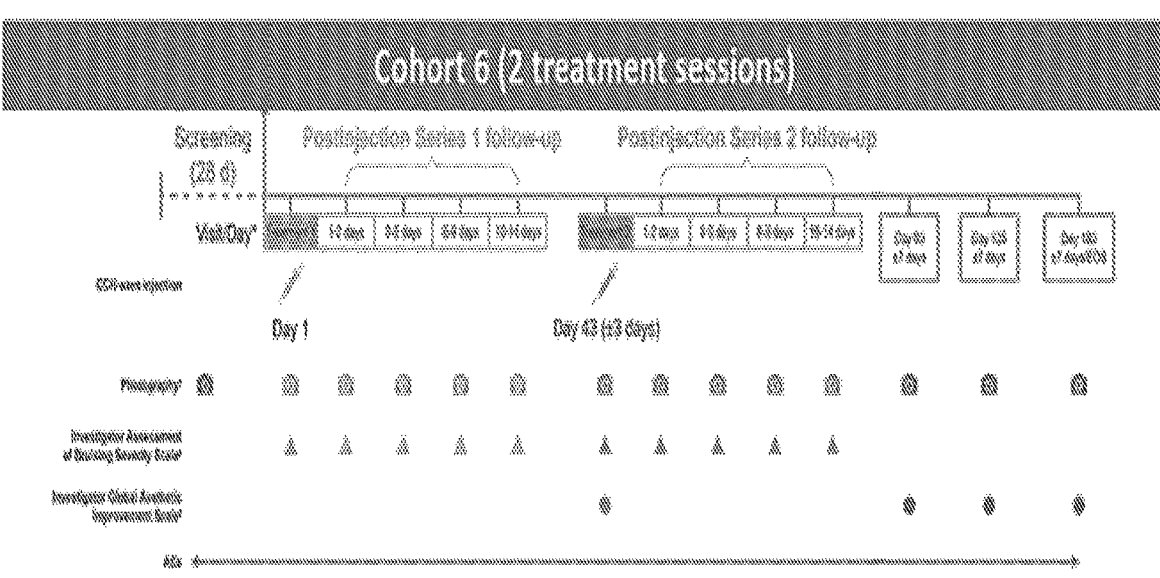

Injection-site bruising (on investigational and control sides) as well as other safety and efficacy parameters were monitored throughout the study. The trial included 4 follow-up visits after each CCH-aaes treatment session (1-2 days, 3-5 days, 6-9 days, and 10-14 days posttreatment) to assess injection-site bruising severity and document the severity using standardized digital photography (FIG. 4A and FIG. 4B).

Ad Hoc and On-Going Assessments

At the time of this filing, enrollment in the study was complete but not all follow-up visits had occurred. An ad hoc assessment was performed on the data generated from the follow-up visits that were completed as of that date. Bruising severity will be/was determined via live assessment using the 5-point Investigator Assessment of Bruising Severity Scale (IABSS), with each buttock individually evaluated to enable comparison (FIG. 2). The primary efficacy endpoint will be/was the proportion of participants whose left buttock (investigational treatment) has an IABSS score at least 1 level lower than that of the right buttock (control treatment) 3-5 days after the first CCH-aaes treatment (second follow-up visit) of Post injection Series 1. Secondary efficacy endpoints will include/included:

The proportion of participants whose left buttock has/had an IABSS score at least 1 level lower than that of the right buttock by visit:

The proportion of participants with a ≥1-level improvement from baseline (Day 1) in Investigator-Global Aesthetic Improvement Scale (I-GAIS) by visit (I-GAIS uses a 7-point scale ranging from +3 ("very much improved") to −3 ("very much worse"))

Adverse events, including injection-site reactions, will be/was monitored in each buttock throughout the study.

Conclusions

APHRODITE-I was designed to determine whether different interventions (i.e., dose, concentration, injection technique, and additional diluent additives) can prevent or reduce injection-site bruising after CCH-aaes treatment for cellulite in the buttocks. This trial was created with the flexibility to add cohorts so additional interventions can be tested over time.

The data provided below is an ad hoc extract of the data gathered as of the time of this filing (prior to the completion of all follow-up visits). Table 6 shows the summary of one-level IABSS responders at visit 2 (Days 1-2 after treatment), visit 3 (Days 3-5 after treatment), and visit 4 (Days 6-9 after treatment) for Cohorts 1-6. For Cohorts 7a and 7b, a comparison of the equivalent visits (visit 2 with visit 7; visit 3 with visit 8; visit 4 with visit 9) for each respective buttock are listed. Although data was collected out to Day 90±7 days the level of bruising after initial treatment began to subside on both the investigational side (left buttock) and control side (right buttock) around visit 4 rendering any visual difference in bruising between the two buttocks negligible. More precisely, bruising began to subside around visit 4 for Cohorts 1-6 and visits 4/9 for Cohorts 7a and 7b (the corresponding visits after initial treatment of each respective buttock). Therefore, only the data from visits 2, 3, and 4 (for Cohorts 1-6) and visits 2 vs. 7/7 vs. 2, 3 vs 8/8 vs 3, and 4 vs. 9/9 vs. 4 (for Cohorts 7a and 7b) are provided herein. As shown in Table 6, at visit 3, over 90% of subjects in Cohort 1 exhibited an at least 1 point improvement on IABSS and over 63% of subjects in Cohort 6 exhibited an at least 1 point improvement on IABSS. The percent of subjects exhibiting an at least 1 point improvement on IABSS at visit 4 was lower than for visit 3 because, as mentioned above, bruising subsided in both the investigational side and control side by visit 4.

Figure 5:
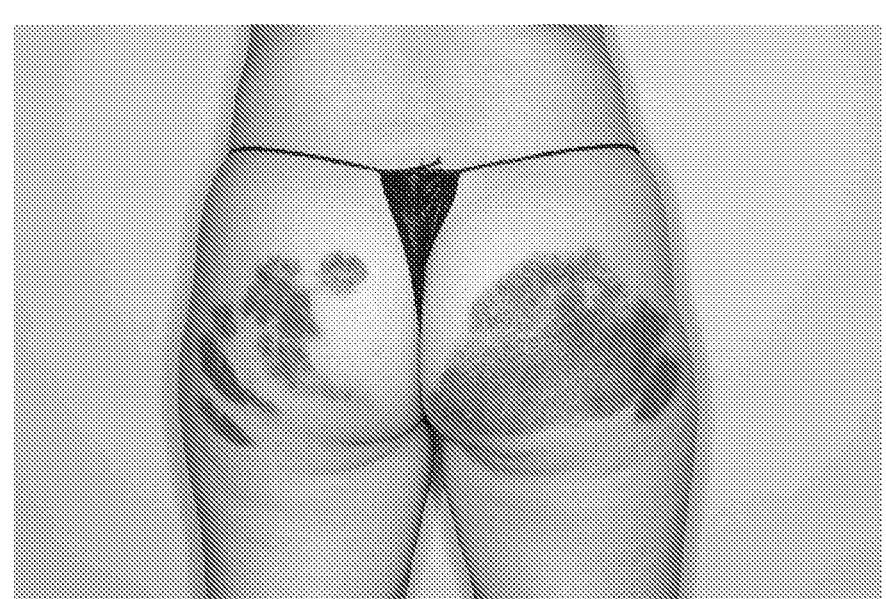
FIG. 5 illustrates the level of bruising observed in a patient from Cohort 1 at Visit 3 (Day 3-5 after treatment). Left buttock (investigational): received 0.42 mg of CCH-aaes having a concentration of 0.23 mg/ml using the three-injection technique. Right buttock (control): received 0.84 mg of CCH-aaes having a concentration of 0.23 mg/ml using the three-injection technique.

FIG. 5 illustrates the level of bruising observed in a patient from Cohort 1 at Visit 3 (Days 3-5 after treatment). The left buttock received 0.42 mg of CCH-aaes having a concentration of 0.23 mg/ml using the three-injection technique, and the right buttock (control) received 0.84 mg of CCH-aaes having a concentration of 0.23 mg/ml using the three-injection technique. As shown in FIG. 5, an at least 1 point improvement on IABSS was observed.

TABLE 6

| Summary of One-Level IABSS Responders By Visit | | | |
|---|---|---|---|
| Visit | One-Level | One-Level IABSS Responders | |
| Cohort | Responder [1] | n (%) | 95% CI [2] |
| Visit 2 | | | |
| Cohort 1 (N = 22) | Yes | 18 (81.8) | 59.72-94.81 |
| | No | 4 (18.2) | |
| | Missing | 0 | |
| Cohort 2 (N = 14) | Yes | 2 (15.4) | 1.92-45.45 |
| | No | 11 (84.6) | |
| | Missing | | |
| Cohort 3 (N = 5) | Yes | 0 (0.0) | 0-52.18 |
| | No | 5 (100.0) | |
| | Missing | 0 | |
| Cohort 4 (N = 7) | Yes | 3 (42.9) | 9.90-81.59 |
| | No | 4 (57.1) | |
| | Missing | 0 | |
| Cohort 5 (N = 10) | Yes | 4 (40.0) | 12.16-73.76 |
| | No | 6 (60.0) | |
| | Missing | 0 | |
| Cohort 6 (N = 19) | Yes | 8 (44.4) | 21.53-69.24 |
| | No | 10 (55.6) | |
| | Missing | 1 | |
| Visit 2 vs Visit 7 | | | |
| Cohort 7a (N = 7) | Yes | 1 (16.7) | 10.42-64.12 |
| | No | 5 (83.3) | |
| | Missing | 1 | |
| Visit 7 vs Visit 2 | | | |
| Cohort 7b (N = 7) | Yes | 3 (42.9) | 9.90-81.59 |
| | No | 4 (57.1) | |
| | Missing | 0 | |
| Visit 3 | | | |
| Cohort 1 (N = 22) | Yes | 19 (90.5) | 69.62-98.83 |
| | No | 2 (9.5) | |
| | Missing | 1 | |
| Cohort 2 (N = 14) | Yes | 3 (25.0) | 5.49-57.19 |
| | No | 9 (75.0) | |
| | Missing | 2 | |
| Cohort 3 (N = 5) | Yes | 1 (20.0) | 0.51-71.64 |
| | No | 4 (80.0) | |
| | Missing | 0 | |
| Cohort 4 (N = 7) | Yes | 2 (33.3) | 4.33-77.72 |
| | No | 4 (66.7) | |
| | Missing | 1 | |
| Cohort 5 (N = 10) | Yes | 4 (44.4) | 13.70-78.80 |
| | No | 5 (55.6) | |
| | Missing | 1 | |
| Cohort 6 (N = 19) | Yes | 12 (63.2) | 38.36-83.71 |
| | No | 7 (36.8) | |
| | Missing | 0 | |
| Visit 3 vs Visit 8 | | | |
| Cohort 7a (N = 7) | Yes | 2 (33.3) | 4.33-77.72 |
| | No | 4 (66.7) | |
| | Missing | 1 | |
| Visit 8 vs Visit 3 | | | |
| Cohort 7b (N = 7) | Yes | 2 (33.3) | 4.33-77.72 |
| | No | 4 (66.7) | |
| | Missing | 1 | |
| Visit 4 | | | |
| Cohort 1 (N = 22) | Yes | 9 (40.9) | 20.71-63.65 |
| | No | 13 (59.1) | |
| | Missing | 0 | |
| Cohort 2 (N = 14) | Yes | 5 (38.5) | 13.86-68.42 |
| | No | 8 (61.5) | |
| | Missing | 1 | |

TABLE 6-continued

| Summary of One-Level IABSS Responders By Visit | | | |
|---|---|---|---|
| Visit | One-Level | One-Level IABSS Responders | |
| Cohort | Responder [1] | n (%) | 95% CI [2] |
| Cohort 3 (N = 5) | Yes | 2 (40.0) | 5.27-83.34 |
| | No | 3 (60.0) | |
| | Missing | 0 | |
| Cohort 4 (N = 7) | Yes | 2 (28.6) | 3.67-70.96 |
| | No | 5 (71.4) | |
| | Missing | 0 | |
| Cohort 5 (N = 10) | Yes | 1 (10.0) | 0.25-44.50 |
| | No | 9 (90.0) | |
| | Missing | 0 | |
| Cohort 6 (N = 19) | Yes | 6 (31.6) | 12.58-56.55 |
| | No | 13 (68.4) | |
| | Missing | 0 | |
| Visit 4 vs Visit 9 | | | |
| Cohort 7a (N = 7) | Yes | 2 (40.0) | 5.27-85.34 |
| | No | 3 (60.0) | |
| | Missing | 2 | |

TABLE 6-continued

| Summary of One-Level IABSS Responders By Visit | | | |
|---|---|---|---|
| Visit | One-Level | One-Level IABSS Responders | |
| Cohort | Responder [1] | n (%) | 95% CI [2] |
| Visit 9 vs Visit 4 | | | |
| Cohort 7b (N = 7) | Yes | 3 (42.9) | 9.90-81.59 |
| | No | 4 (57.1) | |
| | Missing | 0 | |

[1] A one-level IABSS responder at Visit A versus Visit B is defined as the participant whose left buttock (investigational side) at Visit A demonstrates at least a 1-level lower IABSS score versus the right buttock (control side) at Visit B, where Visit A and B can either be same or different.
[2] 95% CI is based on the Clopper-Pearson method of binomial proportion.
Note:
CI = Confidence Interval, IABSS = Investigator Assessment of Bruising Severity Scale.
Percentages are based on the number of participants ('n') with assessment at current visit.
Full Analysis Set (FAS) is defined as all participants in the Safety Population who have at least 1 valid IABSS assessment at a treatment area after an injection of QWO (CCH-aaes).

Example 2—QWO® U.S. Prescribing Information
(QWO® Label)

Provided below is a copy of the FDA approved label for QWO®, which provides the U.S. prescribing information. This label was obtained from www_accessdata.fda.gov/ drupsatfda_docs/label/2020/761146s000lbl.pdf on May 10, 2023.

HIGHLIGHTS OF PRESCRIBING INFORMATION
These highlights do not include all the information needed to use QWO safely and effectively. See full prescribing information for QWO.

QWO™ (collagenase clostridium histolyticum-aaes) for injection, for subcutaneous use
Initial U.S. Approval: 2020

———————————— INDICATIONS AND USAGE ————————————
QWO is a combination of bacterial collagenases indicated for the treatment of moderate to severe cellulite in the buttocks of adult women. (1)

———————————— DOSAGE AND ADMINISTRATION ————————————
- A treatment area is defined as a single buttock receiving up to 12 injections, 0.3 mL each (up to a total of 3.6 mL), of QWO. (2.1)
- A treatment visit may consist of up to 2 treatment areas. Treatment visits should be repeated every 21 days for 3 treatment visits. (2.1)
- Reconstitute QWO lyophilized powder with the supplied diluent prior to use. (2.2)
- Inject 0.84 mg of QWO per treatment area as 12 subcutaneous injections (0.3-mL injection administered as three 0.1-mL aliquots per injection). (2.3)

———————————— DOSAGE FORMS AND STRENGTHS ————————————
For injection: 0.92 mg or 1.84 mg as a lyophilized powder in single-dose vials. (3)

———————————— CONTRAINDICATIONS ————————————
- History of hypersensitivity to any collagenase or to any of the components in the formulation. (4)
- Infection at the injection site. (4)

———————————— WARNINGS AND PRECAUTIONS ————————————
- Hypersensitivity Reactions: Serious hypersensitivity reactions, including anaphylaxis may occur with collagenase clostridium histolyticum. If a serious hypersensitivity reaction occurs, initiate appropriate therapy. (5.1)
- Injection Site Bruising: Bruising occurs frequently after QWO administration. Use with caution in patients with bleeding abnormalities or who are currently being treated with antiplatelet (except those taking ≤ 150 mg aspirin daily) or anticoagulant therapy. (5.2)
- Substitution: QWO must not be substituted for other injectable collagenase products. QWO is not indicated for the treatment of Peyronie's disease or Dupuytren's contracture. (5.3)

———————————— ADVERSE REACTIONS ————————————
The most common adverse reactions (≥ 1%) were related to the injection site (bruising, pain, nodule, pruritus, erythema, discoloration, swelling, and warmth). (6.1)

To report SUSPECTED ADVERSE REACTIONS, contact Endo Pharmaceuticals Inc. at 1-800-462-3636 or FDA at 1-800-FDA-1088 or www.fda.gov/medwatch.

See 17 for PATIENT COUNSELING INFORMATION and FDA-approved patient labeling

Revised: 07/2020

---

FULL PRESCRIBING INFORMATION: CONTENTS*

1    INDICATIONS AND USAGE
2    DOSAGE AND ADMINISTRATION
     2.1   Dosage
     2.2   Reconstitution of Lyophilized Powder
     2.3   Administration
3    DOSAGE FORMS AND STRENGTHS
4    CONTRAINDICATIONS
5    WARNINGS AND PRECAUTIONS
     5.1   Hypersensitivity Reactions
     5.2   Injection Site Bruising
     5.3   Substitution of Collagenase Products
6    ADVERSE REACTIONS
     6.1   Clinical Trials Experience
     6.2   Immunogenicity
     6.3   Postmarketing Experience
8    USE IN SPECIFIC POPULATIONS
     8.1   Pregnancy 8.2   Lactation
     8.4   Pediatric Use
     8.5   Geriatric Use
11   DESCRIPTION
12   CLINICAL PHARMACOLOGY
     12.1  Mechanism of Action
     12.2  Pharmacodynamics
     12.3  Pharmacokinetics
13   NONCLINICAL TOXICOLOGY
     13.1  Carcinogenesis, Mutagenesis, Impairment of Fertility
14   CLINICAL STUDIES
16   HOW SUPPLIED/STORAGE AND HANDLING
17   PATIENT COUNSELING INFORMATION

*Sections or subsections omitted from the full prescribing information are not listed.

FULL PRESCRIBING INFORMATION

1       INDICATIONS AND USAGE

QWO is indicated for the treatment of moderate to severe cellulite in the buttocks of adult women.

2       DOSAGE AND ADMINISTRATION

2.1       Dosage

QWO is injected subcutaneously at a dose of 0.84 mg per treatment area.

- A treatment area is defined as a single buttock receiving up to 12 injections, 0.3 mL each (up to a total of 3.6 mL), of QWO.

- A treatment visit may consist of up to 2 treatment areas.

Treatment should be repeated every 21 days for 3 treatment visits.

2.2       Reconstitution of Lyophilized Powder

Before reconstitution, remove the vials from the refrigerator and let stand at room temperature for at least 15 minutes. Inspect the vials containing QWO. The cake of lyophilized powder should be white in color and intact, showing no signs of erosion. The diluent should be a colorless solution, free of particulate matter.

After removal of the flip-off cap from the vial(s), using aseptic technique swab the rubber stopper and surrounding surface of the vial(s) containing QWO and diluent with sterile alcohol (no other antiseptics should be used).

Use only the supplied diluent for the reconstitution of QWO.

Using an appropriate sized syringe and needle (not supplied), withdraw the amount of supplied diluent based on the number of injection sites (see Table 1).

Table 1:      Reconstitution Instructions for QWO

|  | Single Treatment Area | Two Treatment Areas |
|---|---|---|
| Collagenase clostridium histolyticum-aaes (mg) | 0.92 | 1.84 |
| Volume of diluent (mL) | 4 | 8 |
| Concentration after reconstitution (mg/mL) | 0.23 | 0.23 |
| Number of treatment areas | 1 | 2 |

Inject the diluent slowly into the sides of the vial containing the lyophilized powder of QWO. Do not invert the vial or shake the solution. Slowly swirl the solution to ensure that all of the lyophilized powder has gone into solution.

The reconstituted QWO solution in the vial can be kept at room temperature (20°C to 25°C/68°F to 77°F) for up to 8 hours or refrigerated at 2°C to 8°C (36°F to 46°F) for up to 72 hours prior to administration. If the reconstituted QWO solution in the vial is refrigerated, allow this solution to return to room temperature for approximately 15 minutes before use.

The reconstituted QWO solution should be clear, colorless and free of particulate matter. Inspect the solution visually for particulate matter or discoloration prior to administration. If the reconstituted QWO is not a clear, colorless solution essentially free of particulate matter, do not inject it.

Discard the syringe(s) and needle(s) used for reconstitution and the diluent vial(s).

After reconstitution, QWO solution in the vial should be used for only one injection session and for only one patient.

2.3    Administration

Preparation of Syringes for Injection

Using 1-mL syringes with removable needles (not supplied), draw up 0.9 mL of the reconstituted solution into each syringe. See Table 2 for the appropriate number of syringes needed based on the number of injection sites. After the syringes are prepared, pull the solution remaining in the needles into the barrels of the syringe and then replace the needle with a 30-gauge 1/2-inch needle. Administer reconstituted solution prepared in 1-mL syringes immediately. Do not store reconstituted solution in the 1-mL syringes.

Table 2:        Preparation Instructions for QWO

|  | Single Treatment Visit | Two Treatment Visit |
|---|---|---|
| Number of 1-mL syringes | 4 | 8 |
| Volume per syringe (mL) | 0.9 | 0.9 |
| Amount of collagenase clostridium histolyticum-aaes per syringe (mg) | 0.21 | 0.21 |
| Total injection volume (mL) in prepared syringes | 3.6 | 7.2 |
| Total injection amount of collagenase clostridium histolyticum-aaes (mg) in prepared syringes | 0.84 | 1.68 |

Injection Technique

Mark the injection sites while the patient is standing. Inject QWO subcutaneously while the patient is in a prone position. Each injection of QWO should be administered as three 0.1-mL aliquots to positions A, B, and C (for a total injection volume of 0.3 mL) as shown in the following figure. The depth of the injection should be 0.5 inches (corresponding to the length of the needle) without downward pressure.

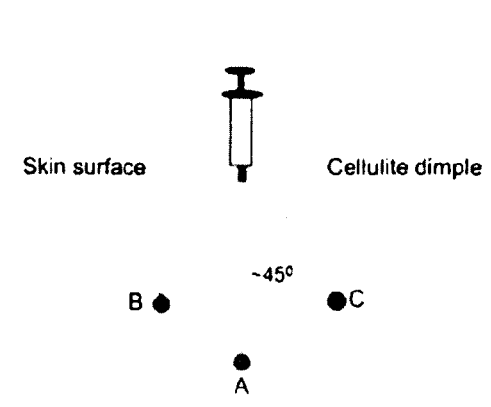

Skin surface        Cellulite dimple

-45°

B ●        ●C

●
A

Needle Tip Position A: Position the needle at 90° angle perpendicular to the skin surface at the injection site and inject one 0.1-mL aliquot by gently pushing on the syringe plunger.

Needle Tip Position B: Withdraw the needle slightly (but not so much as to remove from the injection site) and reposition approximately 45° (but not more than 45°) and inject one 0.1-mL aliquot (towards head).

Needle Tip Position C: Withdraw the needle slightly (but not so much as to remove from the injection site) and reposition approximately 45° (but not more than 45°) and inject one 0.1-mL aliquot, (towards foot).

Withdraw needle from the skin completely and move to the next identified injection site. Each treatment area may receive up 12 injections. After treatment the patient should remain prone for at least 5 minutes.

Do not store, pool, or use any vials or syringes containing unused reconstituted solution after administration. Discard any unused portions.

3        DOSAGE FORMS AND STRENGTHS

For injection: 0.92 mg or 1.84 mg of collagenase clostridium histolyticum-aaes as a lyophilized powder (appearing as a white cake) in single-dose vials.

4        CONTRAINDICATIONS

QWO is contraindicated in:

- patients with a history of hypersensitivity to collagenase or to any of the excipients *[see Warnings and Precautions (5.1)]*.

- the presence of infection at the injection sites.

5        WARNINGS AND PRECAUTIONS

5.1        Hypersensitivity Reactions

Serious hypersensitivity reactions including anaphylaxis have been reported with the use of collagenase clostridium histolyticum. If such a reaction occurs, further injection of QWO should be discontinued and appropriate medical therapy immediately instituted.

5.2        Injection Site Bruising

In clinical trials, 84% of subjects treated with QWO experienced injection site bruising *[see Adverse Reactions (6.1)]*. Subjects with coagulation disorders or using anticoagulant or antiplatelet medications (except those taking ≤ 150 mg aspirin daily) were excluded from participating in Trials 1 and 2.

QWO should be used with caution in patients with bleeding abnormalities or who are currently being treated with antiplatelet (except those taking ≤ 150 mg aspirin daily) or anticoagulant therapy.

5.3    Substitution of Collagenase Products

QWO must not be substituted with other injectable collagenase products. QWO is not intended for the treatment of Peyronie's Disease or Dupuytren's Contracture

6    ADVERSE REACTIONS

The following adverse reactions to QWO for injection are discussed in greater detail in other sections of the labeling:

- Hypersensitivity *[see Contraindications (4) and Warnings and Precautions (5.1)]*.

- Injection Site Bruising *[see Warnings and Precautions (5.2)]*.

6.1    Clinical Trials Experience

Because clinical trials are conducted under widely varying conditions, the adverse reaction rates observed in the clinical trials of a drug cannot be directly compared to rates in the clinical trials of another drug and may not reflect the rates observed in clinical practice.

In two double-blind, placebo-controlled clinical trials (Trials 1 and 2) of identical design, 424 female subjects with cellulite in the buttocks received QWO and 419 female subjects with cellulite received placebo. Enrolled subjects were adults age 18 to 78 years with moderate to severe cellulite (graded as 3 or 4 on a 0 to 4 scale) and without excessive skin laxity. The majority were White (78%) or African American (18%). Subjects completed up to 3 treatment visits separated by 21 days and were followed for up to 6 months after the last treatment visit in a separate open-label extension trial (Trial 3).

Table 3 shows the incidence of adverse reactions that were reported in ≥ 1% of subjects who received QWO-and at a frequency greater than subjects who received placebo in Trials 1 and 2 through Day 71. Generally, adverse reactions had a duration of less than 21 days.

Table 3: Adverse Reactions Occurring in ≥ 1% of Subjects in Trials 1 and 2 Through Day 71

| Adverse Reactions at Injection Site | QWO<br>N=424<br>% | Placebo<br>N=419<br>% |
|---|---|---|
| Bruising | 84 | 21 |
| Pain | 48 | 10 |
| Nodule | 33 | 1 |
| Pruritus | 15 | 1 |
| Erythema | 9 | 5 |
| Discoloration | 8 | 1 |
| Swelling | 8 | 1 |
| Warmth | 3 | 0 |

Pooled terms:
- Bruising - injection site bruising, injection site hematoma, and injection site hemorrhage (refers to verbatim term injection site ecchymosis)
- Pain - injection site pain, injection site discomfort, and injection site dysesthesia
- Swelling - injection site swelling, injection site edema, injection site induration
- Discoloration - injection site discoloration
- Nodule- injection site mass and injection site nodule Four hundred seventy-nine (479) subjects from Trials 1 and 2 completed a 6-month observation phase in the ongoing open-label safety extension (Trial 3). No long-term safety signals have been identified.

6.2    Immunogenicity

As with all therapeutic proteins, there is potential for immunogenicity. The detection of antibody formation is highly dependent on the sensitivity and specificity of the assay. Additionally, the observed incidence of antibody (including neutralizing antibody) positivity in an assay may be influenced by several factors including assay methodology, sample handing, timing of sample collection, concomitant medications, and underlying disease. For these reasons, comparison of the incidence of antibodies in the studies described below with the incidence of antibodies in other studies or to other products, including other collagenase clostridium histolyticum products, may be misleading.

By Day 22, approximately 53% (203/383) and 26% (101/383) of subjects who completed the first treatment visit of QWO at the recommended dose in Trials 1 and 2 developed anti-AUX-I and anti-AUX-II antibodies, respectively. The majority (> 96%) of subjects developed antibodies for AUX-I and AUX-II after second and third treatment visits. Antibody titers suggested that antibodies were retained for up to 360 days after receiving the first recommended dose. By Day 71, approximately 68% and 83% of subjects developed antibodies to AUX-I and AUX-II which were classified as neutralizing, respectively.

Antibodies to AUX-I and AUX-II including those classified as neutralizing were not associated with changes in clinical response or adverse reactions at injection site.

6.3      Postmarketing Experience

Because adverse reactions are reported voluntarily from a population of uncertain size, it is not always possible to reliably estimate their frequency or establish a causal relationship to drug exposure. The following adverse reaction was reported during post approval use of a collagenase product:

> Immune system disorders: serious hypersensitivity reactions including anaphylaxis*[see Warnings and Precautions (5.1)]*.

8      USE IN SPECIFIC POPULATIONS

8.1      Pregnancy

Risk Summary

There are no available data on collagenase clostridium histolyticum use in pregnant women to evaluate for a drug- associated risk of major birth defects, miscarriage or adverse maternal or fetal outcomes. Following subcutaneous injection, the systemic concentrations for QWO were below the bioanalytical assay limit of quantification *[see Clinical Pharmacology (12.3)]*.

In animal reproduction studies, intravenous administration of collagenase clostridium histolyticum to pregnant rats during organogenesis at doses up to 0.13 mg/rat (43 × human equivalent dose [HED] on a mg/kg basis) revealed no evidence of harm to the fetus.

The estimated background risk of major birth defects and miscarriage for the indicated population is unknown. All pregnancies have a background risk of birth defect, loss, or other adverse outcomes. In the US general population, the estimated background risk of major birth defects and miscarriage in clinically recognized pregnancies is 2-4% and 15-20%, respectively.

8.2      Lactation

Risk Summary

There are no data on the presence of collagenase clostridium histolyticum in human milk, the effects of collagenase clostridium histolyticum on the breastfed child or on milk production. Following subcutaneous injection, the systemic concentrations for QWO were below the bioanalytical assay limit of quantification [see *Clinical Pharmacology (12.3)*]. The developmental and health benefits of breastfeeding should be considered along with the mother's clinical need for collagenase clostridium histolyticum and any potential adverse effects on the breastfed child from collagenase clostridium histolyticum, or from the underlying maternal condition.

8.4      Pediatric Use

The safety and effectiveness of QWO have not been established in pediatric patients.

8.5 Geriatric Use

In two double-blind, placebo-controlled, clinical trials in subjects with cellulite (Trials 1 and 2), 24 (5.7%) of the 424 subjects who received QWO were 65 years of age or older. No overall differences in safety of QWO were observed between these patients and younger patients.

11 DESCRIPTION

Collagenase clostridium histolyticum-aaes is a combination of bacterial collagenases AUX-I and AUX-II, in an approximate 1:1 mass ratio, which are isolated and purified from the fermentation of Clostridium histolyticum bacteria.

Collagenase AUX-I is a single polypeptide chain consisting of approximately 1000 amino acids. It has an observed molecular weight of 114 kiloDaltons (kDa). It belongs to the class I Clostridium histolyticum collagenases.

Collagenase AUX-II is a single polypeptide chain consisting of approximately 1000 amino acids. It has an observed molecular weight of 113 kDa. It belongs to the class II Clostridium histolyticum collagenases.

QWO (collagenase clostridium histolyticum-aaes) for injection is supplied as a sterile, preservative-free, lyophilized powder (appearing as a white cake) in single-dose vials for subcutaneous use after reconstitution with the Diluent for QWO.

Each QWO 0.92-mg single-dose vial contains 0.92 mg of collagenase clostridium histolyticum-aaes and mannitol (37.7 mg), sucrose (18.9 mg), tromethamine (1.1 mg), and hydrochloric acid as needed to adjust pH. Reconstitution with 4 mL of supplied Diluent for QWO yields a solution containing 0.23 mg/mL collagenase clostridium histolyticum-aaes at a pH of approximately 8.0.

Each QWO 1.84-mg single-dose vial contains 1.84 mg of collagenase clostridium histolyticum-aaes and mannitol (75.4 mg), sucrose (37.8 mg), tromethamine (2.2 mg), and hydrochloric acid as needed to adjust pH. Reconstitution with 8 mL of supplied Diluent for QWO yields a solution containing 0.23 mg/mL collagenase clostridium histolyticum-aaes at a pH of approximately 8.0.

Diluent for QWO is a sterile, preservative-free, colorless solution in a single-dose vial containing either 4 mL or 8 mL of 0.03% calcium chloride dihydrate in 0.6% sodium chloride, and Water for Injection, USP.

12 CLINICAL PHARMACOLOGY

12.1 Mechanism of Action

Collagenases are proteinases that hydrolyze collagen in its native triple helical conformation under physiological conditions. The exact mechanism for the treatment of moderate to severe cellulite is unknown.

12.2 Pharmacodynamics

Pharmacodynamics of QWO are unknown.

12.3    Pharmacokinetics

Pharmacokinetics of collagenases clostridium histolyticum were evaluated in 140 female subjects with cellulite in four clinical trials. Plasma concentrations of clostridium type I collagenase (AUX-I) and clostridium type II collagenase (AUX-II) were below the lower limit of quantitation of 5 ng/mL and 25 ng/mL, respectively, in all subjects that received a single dose of (QWO) up to 3.36 mg in up to 4 treatment areas (up to 0.84 mg per treatment area).

13    NONCLINICAL TOXICOLOGY

13.1    Carcinogenesis, Mutagenesis, Impairment of Fertility

Long-term animal studies to evaluate the carcinogenic potential of collagenase clostridium histolyticum have not been conducted.

Purified collagenase clostridium histolyticum was not mutagenic in *Salmonella typhimurium* (Ames test) and was not clastogenic in both an in vivo mouse micronucleus assay and an in vitro chromosomal aberration assay in human lymphocytes.

Collagenase clostridium histolyticum did not impair fertility and early embryonic development when administered intravenously to rats at doses up to 0.13 mg/rat (43 × HED on a mg/kg basis).

14    CLINICAL STUDIES

Two randomized, multicenter, double-blind, placebo-controlled trials, Trial 1 and Trial 2, of identical design were conducted to evaluate safety and efficacy of QWO for the treatment of cellulite in adult women. Eligible subjects had cellulite severity in both buttocks of moderate (3) to severe (4) as evaluated on 5-level scales (0=none; 4=severe) by both the subject, using the Patient Reported Photonumeric Cellulite Severity Scale (PR-PCSS), and the investigator, using the Clinician Reported Photonumeric Cellulite Severity Scale (CR-PCSS).

A dose of 0.84 mg of QWO per buttock was administered as 12 subcutaneous injections (0.3-mL injection administered as three 0.1-mL aliquots per injection) in each of 2 buttocks for a total dose of 1.68 mg and a total volume of 7.2 mL (3.6 mL per buttock) per treatment visit. There were 3 treatment visits at 21-day intervals.

In Trials 1 and 2, the primary efficacy endpoint was the proportion of 2-level multi-component responders at Day 71 post randomization. A 2-level multi-component responder was defined as having an improvement of at least 2 levels of cellulite severity from baseline on both the CR-PCSS and the PR-PCSS in the target buttock.

Patient satisfaction with the appearance of their cellulite was assessed using a patient reported outcome scale ranging from 0 (extremely dissatisfied) to 6 (extremely satisfied).

The mean age was 47 years with a mean BMI of 31 kg/m². All of the subjects were female, and most were White (78%). At baseline, 61% subjects had investigator reported cellulite severity (CR-PCSS) scores of moderate and 39% subjects had cellulite severity scores of severe.

Reductions in cellulite severity were observed more frequently in the QWO group compared to the placebo group as measured by the investigator (CR-PCSS) and patient (PR-PCSS) scales at Day 71 (Table 4).

Table 4: Subject/Investigator 2-Level Responder Analysis at Day 71

| | Trial 1 | | | Trial 2 | | |
|---|---|---|---|---|---|---|
| | QWO N=210 | Placebo N=213 | Adj Trt Diff (95% CI) | QWO N=214 | Placebo N=206 | Adj Trt Diff (95% CI) |
| 2-level multi-component responder | 16 (8%) | 4 (2%) | 6% (2%, 10%) | 12 (6%) | 1 (< 1%) | 5% (2%, 8%) |
| 2-level PR-PCSS responder | 51 (24%) | 26 (12%) | 12% (5%, 19%) | 45 (21%) | 12 (6%) | 15% (9%, 22%) |
| 2-level CR-PCSS responder | 35 (17%) | 12 (6%) | 11% (5%, 17%) | 32 (15%) | 3 (1%) | 13% (8%, 19%) |

Adj Trt Diff=Adjusted treatment difference; CI=Confidence interval

Non-responder imputation used to handle missing data. Adjusted treatment difference is the weighted average of the treatment differences in response percentages across the analysis centers using Cochran-Mantel-Haenszel (CMH) weights along with the associated CI.

In Trials 1 and 2, the measure of patient-reported satisfaction with cellulite appearance showed a greater improvement in the QWO group over the placebo group.

16  HOW SUPPLIED/STORAGE AND HANDLING

How Supplied

QWO (collagenase clostridium histolyticum-aaes) for injection is a sterile, preservative-free, lyophilized powder (appearing as a white cake) in single-dose vials for subcutaneous use.

| NDC Number | Package Size |
|---|---|
| 73611-300-05 | Single treatment area: Carton containing one QWO 0.92-mg single-dose vial and one Diluent for QWO 4-mL single-dose vial [see Description (11)] |
| 73611-300-10 | Two treatment areas: Carton containing one QWO 1.84-mg single-dose vial and one Diluent for QWO 8-mL single-dose vial [see Description (11)] |

Storage and Handling

Refrigerate QWO and Diluent for QWO vials at 2°C to 8°C (36°F to 46°F). Do not freeze.

17  PATIENT COUNSELING INFORMATION

Advise the patient to read the FDA-approved patient labeling (Patient Information).

Hypersensitivity

Advise patients to seek immediate medical attention if they experience any symptoms of serious hypersensitivity reactions *[see Warnings and Precautions (5.1)]*.

Injection Site Bruising

Advise patients that injection site bruising may occur with administration of QWO *[see Warnings and Precautions (5.2)]*.

Manufactured by:
Endo Global Aesthetics Limited
Dublin, Ireland
US License No. 2136

Distributed by:
Endo Aesthetics LLC
Malvern, PA 19355

| Patient Information<br>QWO (kwoe)<br>(collagenase clostridium histolyticum-aaes)<br>for injection, for subcutaneous use |
|---|

What is QWO?

QWO is a prescription medicine used for the treatment of moderate to severe cellulite in the buttocks of adult women.

It is not known if QWO is safe and effective in children.

Do not receive QWO if you:

- Are allergic to any collagenase or to any of the ingredients in QWO. See the end of this Patient Information for a complete list of ingredients in QWO.
- Have an active infection in the treatment area.

Before receiving QWO, tell your healthcare provider about all of your medical conditions, including if you:

- have had an allergic reaction to a QWO injection in the past
- have a bleeding problem
- are pregnant or plan to become pregnant. It is not known if QWO will harm your unborn baby.
- are breastfeeding or plan to breastfeed. It is not known if QWO passes into your breast milk. Talk to your healthcare provider about the best way to feed your baby if you receive QWO.

Tell your healthcare provider about all the medicines you take, including prescription and over-the-counter medicines, vitamins, and herbal supplements. Especially tell your healthcare provider if you take a medicine that prevents the clotting of your blood (antiplatelet or anticoagulant medicine).

How will I receive QWO?

- QWO is injected into the fat (subcutaneously) of each single buttock (treatment area) by your healthcare provider. You may receive up to 12 injections per treatment area.
- Each treatment visit may include up to 2 treatment areas.
- QWO injections will be given 21 days apart for 3 treatment visits.

What are the possible side effects of QWO?

QWO may cause serious side effects, including:

- Allergic (hypersensitivity) reactions, including anaphylaxis. Call your healthcare provider right away if you have any of these symptoms of an allergic reaction after an injection of QWO:

| | |
  |---|---|
  | o   hives | o   swollen face |
  | o   trouble breathing | o   chest pain |
  | o   low blood pressure | o   dizziness or fainting |

- Injection site bruising.

The most common side effects of QWO include bruising, pain, areas of hardness, itching, redness, discoloration, swelling and warmth in the treatment area.

These are not all of the possible side effects of QWO.

Call your doctor for medical advice about side effects. You may report side effects to FDA at 1-800-FDA-1088.

General information about QWO

Medicines are sometimes prescribed for purposes other than those listed in a Patient Information leaflet. If you would like more information, talk to your healthcare provider. You can ask your pharmacist or healthcare provider for more information about QWO that is written for health professionals.

What are the ingredients in QWO?

Active ingredient: collagenase clostridium histolyticum

Inactive ingredients: mannitol, sucrose, tromethamine, and hydrochloric acid The diluent contains: calcium chloride dihydrate, sodium chloride, and Water for Injection, USP Manufactured by: Endo Global Aesthetics Limited, Dublin, Ireland US license number 2136 Distributed by: Endo Aesthetics LLC , Malvern, PA 19355

This Patient Information has been approved by the U.S. Food and Drug Administration                                     Issued: 07/2020

Those skilled in the art will appreciate that numerous changes and modifications can be made to the preferred embodiments disclosed herein and that such change; and modifications can be made without departing from the spirit of the invention. It is, therefore, intended that the appended claims cover all such equivalent variations as fall within the true spirit and scope of the invention.

The disclosures of each patent, patent application, and publication cited or described in this document are hereby incorporated herein by reference, in its entirety.

EMBODIMENTS

The following list of embodiments is intended to complement, rather than displace or supersede, the previous descriptions.

Embodiment 1. A method of reducing collagenase-mediated bruising in a subject having cellulite, the method comprising:

subcutaneously administering to a treatment area of the subject a total dose of about 0.42 mg of collagenase per treatment session to thereby reduce the collagenase-mediated bruising in the subject.

Embodiment 2. The method of embodiment I, wherein the collagenase is administered using a three-injection technique.

Embodiment 3. The method of embodiment I or 2, wherein the collagenase is administered at a depth of about 0.5 inches.

Embodiment 4. The method of any one of embodiments 1-3, wherein the bruising is reduced compared to a level of bruising associated with subcutaneously administering to the treatment area of the subject a total dose of about 0.84 mg of collagenase per treatment session using the three-injection technique at a depth of 0.5 inches.

Embodiment 5. The method of any one of embodiments 1-4, wherein the collagenase has a concentration of about 0.23 mg/ml.

Embodiment 6. A method of reducing collagenase-mediated bruising in a subject having cellulite, the method comprising:

subcutaneously administering to a treatment area of the subject a total dose of about 0.84 mg of collagenase per treatment session, the collagenase having a concentration of about 0.05 mg/ml, to thereby reduce the collagenase-mediated bruising in the subject.

Embodiment 7. The method of embodiment 6, wherein the collagenase is administered using a three-injection technique.

Embodiment 8. The method of embodiment 6 or 7, wherein the collagenase is administered at a depth of about 0.5 inches.

Embodiment 9. The method of any one of embodiments 6-8, wherein the bruising is reduced compared to a level of bruising associated with subcutaneously administering to the treatment area of the subject a total dose of about 0.84 mg of collagenase per treatment session, the collagenase having a concentration of about 0.23 mg/ml, using the three-injection technique at a depth of about 0.5 inches.

Embodiment 10. A method of reducing collagenase-mediated bruising in a subject having cellulite, the method comprising:

subcutaneously administering to a treatment area of the subject a total dose of about 0.84 mg of collagenase per treatment session at a depth of about 0.25 inches to thereby reduce the collagenase-mediated bruising in the subject.

Embodiment 11. The method of embodiment 10, wherein the collagenase is administered using a three-injection technique.

Embodiment 12. The method of embodiment 10 or 11, wherein the bruising is reduced compared to a level of bruising associated with subcutaneously administering to the treatment area of the subject a total dose of about 0.84 mg of collagenase per treatment session using the three-injection technique at a depth of about 0.5 inches.

Embodiment 13. The method of any one of embodiments 10-12, wherein the collagenase has a concentration of about 0.23 mg/ml.

Embodiment 14. A method of reducing collagenase-mediated bruising in a subject having cellulite, the method comprising:

subcutaneously administering to a treatment area of the subject a total dose of about 0.84 mg of collagenase per treatment session, the collagenase having a concentration of about 0.09 mg/ml, to thereby reduce the collagenase-mediated bruising in the subject.

Embodiment 15. The method of embodiment 14, wherein the collagenase is administered using a single aliquot injection.

Embodiment 16. The method of embodiment 14 or 15, wherein the collagenase is administered at a depth of about 0.25 inches.

Embodiment 17. The method of any one of embodiments 14-16, wherein the administering comprises up to 30 single aliquot injections of the collagenase per treatment session.

Embodiment 18. The method of any one of embodiments 14-17, wherein the bruising is reduced compared to a level of bruising associated with subcutaneously administering to the treatment area of the subject a total dose of about 0.84 mg of collagenase per treatment session, the collagenase having a concentration of about 0.23 mg/ml, using the single aliquot injection at a depth of about 0.25 inches.

Embodiment 19. The method of any one of embodiments 14-18, wherein the administering comprises up to 12 single aliquot injections of the collagenase per treatment session.

Embodiment 20. The method of any one of embodiments 14-19, wherein the injections are spaced about 2 cm to about 3 cm apart.

Embodiment 21. The method of embodiment 20, wherein the injections are spaced in a grid pattern.

Embodiment 22. A method of reducing collagenase-mediated bruising in a subject having cellulite, the method comprising:

subcutaneously administering to a treatment area of the subject a composition comprising collagenase, lidocaine, and epinephrine, wherein a total dose of about 0.42 mg of the collagenase is administered per treatment session to thereby reduce the collagenase-mediated bruising in the subject.

Embodiment 23. The method of embodiment 22, wherein the collagenase is administered using a three-injection technique.

Embodiment 24. The method of embodiment 22 or 23, wherein the collagenase is administered at a depth of about 0.5 inches.

Embodiment 25. The method of any one of embodiments 22-24, wherein the bruising is reduced compared to a level of bruising associated with subcutaneously administering to the treatment area of the subject a composition comprising the collagenase, wherein a total dose of about 0.84 mg of the collagenase is administered per treatment session using a three-injection technique at a depth of about 0.5 inches.

Embodiment 26. The method of any one of embodiments 22-25, wherein the collagenase has a concentration of about 0.23 mg/ml.

Embodiment 27. The method of any one of the previous embodiments, wherein the subject receives multiple treatment sessions.

Embodiment 28. The method of embodiment 27, wherein the treatment sessions are 3 weeks apart.

Embodiment 29. A method of reducing collagenase-mediated bruising in a subject having cellulite, the method comprising:

subcutaneously administering to a treatment area of the subject a total dose of about 0.21 mg of collagenase per treatment session, the collagenase having a concentration of about 0.12 mg/ml, to thereby reduce the collagenase-mediated bruising in the subject.

Embodiment 30. The method of embodiment 29, wherein the collagenase is administered using a three-injection technique.

Embodiment 31. The method of embodiment 29 or 30, wherein the collagenase is administered at a depth of about 0.5 inches.

Embodiment 32. The method of any one of embodiments 29-31, wherein the bruising is reduced compared to a level of bruising associated with subcutaneously administering to the treatment area of the subject a total dose of about 0.42 mg of collagenase per treatment session, the collagenase having a concentration of about 0.23 mg/ml, using the three-injection technique at a depth of about 0.5 inches.

Embodiment 33. The method of any one of embodiments 29-32, wherein the subject receives more than one treatment session that are about 42 days apart.

Embodiment 34. A method of reducing collagenase-mediated bruising in a subject having cellulite, the method comprising:

orally administering to the subject tranexamic acid and subcutaneously administering to a treatment area of the subject a total dose of about 0.84 mg of collagenase per treatment session to thereby reduce the collagenase-mediated bruising in the subject.

Embodiment 35. The method of embodiment 34, wherein the collagenase is administered using a three-injection technique.

Embodiment 36. The method of embodiment 34 or 35, wherein the collagenase is administered at a depth of about 0.5 inches.

Embodiment 37. The method of any one of embodiments 34-36, comprising administering to the subject about 500 mg to about 1500 mg of the tranexamic acid.

Embodiment 38. The method of embodiment 37, comprising administering to the subject about 1300 mg of the tranexamic acid.

Embodiment 39. The method of any one of the previous embodiments, wherein the collagenase is administered in a composition comprising the collagenase, mannitol, sucrose, and tromethamine.

Embodiment 40. The method of any one of the previous embodiments, wherein the level of bruising is evaluated using an Investigator Assessment of Bruising Severity Scale (IABSS).

Embodiment 41. A method of treating cellulite in a subject, the method comprising:

a) subcutaneously administering to a treatment area of the subject a total dose of about 0.42 mg of collagenase per treatment session to thereby treat the cellulite in the subject;

b) subcutaneously administering to a treatment area of the subject a total dose of about 0.84 mg of collagenase per treatment session, the collagenase having a concentration of about 0.05 mg/ml, to thereby treat the cellulite in the subject;

c) subcutaneously administering to a treatment area of the subject a total dose of about 0.84 mg of collagenase per treatment session, the collagenase having a concentration of about 0.23 mg/ml, at a depth of about 0.25 inches to thereby treat the cellulite in the subject;

d) subcutaneously administering to a treatment area of the subject a total dose of about 0.84 mg of collagenase per treatment session, the collagenase having a concentration of about 0.09 mg/ml, to thereby treat the cellulite in the subject;

e) subcutaneously administering to a treatment area of the subject a composition comprising collagenase, lidocaine, and epinephrine, wherein a total dose of about 0.42 mg of the collagenase is administered per treatment session to thereby treat the cellulite in the subject;

f) subcutaneously administering to a treatment area of the subject a total dose of about 0.21 mg of collagenase per treatment session, the collagenase having a concentration of about 0.12 mg/ml, to thereby treat the cellulite in the subject; or g) orally administering to the subject tranexamic acid and subcutaneously administering to a treatment area of the subject a total dose of about 0.84 mg of collagenase per treatment session to thereby treat the cellulite in the subject.

Embodiment 42. The method of embodiment 41, wherein the collagenase is administered using a three-injection technique.

Embodiment 43. The method of embodiment 41, wherein the collagenase is administered using a single aliquot injection.

Embodiment 44. The method of embodiment 42 or 43, wherein the collagenase is administered at a depth of about 0.25 inches or about 0.5 inches.

Embodiment 45. The method of any one of embodiments 41-44, wherein the tranexamic acid in step g) has a concentration of about 500 mg to about 1500 mg.

Embodiment 46. The method of embodiment 45, wherein the tranexamic acid in step g) has a concentration of about 1300 mg.

Embodiment 47. The method of any one of embodiments 41-46, wherein the collagenase is administered in a composition comprising the collagenase, mannitol, sucrose, and tromethamine.

Embodiment 48. The method of embodiment 41, wherein the collagenase in part a) has a concentration of about 0.23 mg/ml.

Embodiment 49. The method of embodiment 41, wherein the injections in part d) are spaced about 2 cm to about 3 cm apart.

Embodiment 50. The method of embodiment 49, wherein the injections are spaced in a grid pattern.

Embodiment SI. The method of any one of embodiments 41-50, wherein the subject receives multiple treatment sessions.

Embodiment 52. The method of embodiment SI, wherein the treatment sessions are 3 weeks apart.

Embodiment 53. The method of embodiment 51, wherein the treatment sessions are about 42 days apart.

Embodiment 54. The method of any one of embodiments 41-53, wherein the treating is established by a scale or measurement tool selected from Hexsel Cellulite Severity Scale (Hexsel CSS), Hexsel Depression Depth Score, Likert Scale, Dimple Analysis, Clinician Reported Photonumeric Cellulite Severity Scale (CR-PCSS). Patient Reported Photonumeric Cellulite Severity Scale (PR-PCSS). Investigator Global Aesthetic Improvement Scale (1-GAIS), Subject Global Aesthetic Improvement Scale (S-GAIS). Patient Reported Cellulite Impact Scale (PR-CIS), PR-CIS Abbreviated. Subject Self-Rating Scale (SSRS). Subject Satisfaction with Cellulite Treatment (SSCT), Clinician assessment of cellulite severity (photography or other imagery). Body-Q, and a validated photonumeric or other scale used by clinicians and/or patients to assess cellulite severity, improvement, and/or patient satisfaction.

Embodiment 55. The method of any one of the previous embodiments, wherein the collagenase comprises a collagenase I, collagenase II, or a mixture of collagenase I and collagenase II.

Embodiment 56. The method of embodiment 55, wherein the collagenase comprises a mixture of collagenase I and collagenase II.

Embodiment 57. The method of embodiment 56, wherein the collagenase I comprises the amino acid sequence of SEQ ID NO: 1 and the collagenase II comprises the amino acid sequence of SEQ ID NO: 2.

Embodiment 58. The method of any one of the previous embodiments, wherein the collagenase is collagenase *Clostridium histolyticum* (CCII).

Embodiment 59. The method of any one of the previous embodiments, wherein the treatment area is the left buttock, the right buttock, or both the left buttock and the right buttock.

Embodiment 60. A formulation comprising:

a collagenase;

lidocaine; and epinephrine.

Embodiment 61. The formulation of embodiment 60, comprising:

about 0.23 mg/ml of collagenase;

about 2% of lidocaine; and about 1:200,000 epinephrine.

Embodiment 62. The formulation of embodiment 60 or 61, wherein the collagenase comprises a collagenase I, collagenase II, or a mixture of collagenase I and collagenase HI.

Embodiment 63. The formulation of embodiment 62, wherein the collagenase comprises a mixture of collagenase I and collagenase II.

Embodiment 64. The formulation of embodiment 63, wherein the collagenase I comprises the amino acid sequence of SEQ ID NO: 1 and the collagenase II comprises the amino acid sequence of SEQ ID NO: 2.

Embodiment 65. The formulation of any one of embodiments 60-64, wherein the collagenase is collagenase *Clostridium histolyticum* (CCH).

---

What is claimed:

1. A method of reducing bruising and/or skin discoloration associated with collagenase-mediated treatment of cellulite in a subject, the method comprising:

subcutaneously administering to a treatment area of the subject a total dose of about 0.42 mg of collagenase per treatment session to thereby reduce the bruising and/or skin discoloration associated with the collagenase-mediated treatment of cellulite in the subject, wherein the subject experiences an at least 1 level improvement on an Investigator Assessment of Bruising Severity Scale (IABSS).

2. The method of claim 1, wherein the collagenase is administered using a three-injection technique.

3. The method of claim 2, wherein the collagenase is administered at a depth of about 0.5 inches.

4. The method of claim 1, wherein the collagenase has a concentration of about 0.23 mg/ml.

5. The method of claim 1, wherein the subject receives multiple treatment sessions.

6. The method of claim 5, wherein the treatment sessions are 3 weeks apart.

7. The method of claim 1, wherein the collagenase is administered in a composition comprising the collagenase, mannitol, sucrose, and tromethamine.

8. The method of claim 1, wherein the collagenase comprises a collagenase I, a collagenase II, or a mixture of collagenase I and collagenase II.

9. The method of claim 8, wherein the collagenase comprises the mixture of collagenase I and collagenase II.

10. The method of claim 9, wherein the collagenase I comprises the amino acid sequence of SEQ ID NO: 1 and the collagenase II comprises the amino acid sequence of SEQ ID NO: 2.

11. The method of claim 8, wherein the collagenase is collagenase *Clostridium histolyticum* (CCH).

* * * * *